(12) United States Patent
Vainstein et al.

(10) Patent No.: US 7,129,393 B1
(45) Date of Patent: Oct. 31, 2006

(54) TRANSGENIC PLANTS AND METHOD FOR TRANSFORMING CARNATIONS

(75) Inventors: Alexander Vainstein, Rehovot (IL);
Amir Zuker, Nes Ziona (IL);
Marianna Ovadis, Rehovot (IL)

(73) Assignee: Yissum Research Development Company of the Hebrew University, Jerusalem (IL)

( * ) Notice: Subject to any disclaimer, the term of this patent is extended or adjusted under 35 U.S.C. 154(b) by 0 days.

(21) Appl. No.: 09/914,146

(22) PCT Filed: Feb. 22, 2000

(86) PCT No.: PCT/IL00/00110

§ 371 (c)(1),
(2), (4) Date: Jan. 29, 2002

(87) PCT Pub. No.: WO00/50613

PCT Pub. Date: Aug. 31, 2000

Related U.S. Application Data

(60) Provisional application No. 60/121,239, filed on Feb. 22, 1999.

(51) Int. Cl.
*C12N 15/82* (2006.01)
*C12N 15/90* (2006.01)
*C12N 15/84* (2006.01)
*A01H 5/00* (2006.01)

(52) U.S. Cl. .................. 800/286; 435/468; 800/296; 800/323.3

(58) Field of Classification Search ............... 800/278, 800/285, 286, 294, 293, 323.3; 435/468, 435/419; 536/23.1
See application file for complete search history.

(56) References Cited

U.S. PATENT DOCUMENTS 6,570,064 B1 * 5/2003 Allen et al. ................. 800/278

FOREIGN PATENT DOCUMENTS

| AU | WO93/20206 | * | 3/1993 |
|---|---|---|---|
| EP | 0 486 233 | | 5/1992 |
| WO | WO 92/17056 | | 10/1992 |
| WO | WO 93/18142 | | 9/1993 |
| WO | WO 94/28140 | | 12/1994 |
| WO | WO 95/06741 | | 3/1995 |
| WO | WO 96/20595 | | 7/1996 |
| WO | WO 96/36716 | | 11/1996 |
| WO | WO 96/39827 | | 12/1996 |
| WO | WO 97/15584 | | 5/1997 |
| WO | WO 97/21816 | | 6/1997 |
| WO | WO 97/35471 | | 10/1997 |
| WO | WO 98/50570 | | 11/1998 |
| WO | WO 99/37794 | | 7/1999 |

OTHER PUBLICATIONS

Bidney et al. Microprojectile bombardment of plant tissues increases transformation frequency by *Agrobacterium tumefaciens*. 1992. Plant Molecular Biology. 18:301-313.*
Van der Krol et al. An anti-sense chalcone synthase gene in transgenic plants inhibits flower pigmentation. 1988. Nature. 333:866-869.*
Lu et al. *Agrobacterium*-mediated transformation of carnation (*Dianthus caryophyllus* L.). 1991. Bio/Technology. 9:864-868.*
Vainstein et al. 2001. Plant Physiol. vol. 127, pp. 1383-1389.*
Gura et al. 2000. Nature. vol. 404, pp. 804-808.*
Holton et al. The Plant Cell. vol. 7, pp. 1071-1083.*
Araneda et al. Nature Neuroscience. 2000. vol. 3(12), pp. 1248-1255.*
Zuker et al., 2002, Mol. Breed., vol. 9, pp. 33-41.*
M. Ovadis, et al. *A highly efficient procedure for generating carnation plants with novel traits*. Proceedings of the Nineteenth International Symposium on Improvement of Ornamental Plants. Breeding Ornamentals in the Future: Goals, Genes, Tools, Angers, France, Jul. 27-30, 1998. ACTA Horticulture (2000) 508:49-51.
M. Ovadis, et al. *Generation of transgenic carnation plants with novel characterisitcs by combining microprojectile bombardment with Agrobacterium tumefaciens transformation*. Current Plant Science and Biotechnology in Agriculture 36:189-192.
A. Zuker, et al. *A highly efficient method for carnation transformation*. ACTA Horticulture (1997) 447:373-375.
E. Firoozabady, et al. *Efficient transformation and regeneration of carnation cultivars using Agrobacterium*. Molecular Breeding (1995) 1:283-293.
Tanaka Toshikazu, et al. *Metabolic engineering to modify flower color*. Plant and Cell Physiology 39(11):1119-1126.
J. Dedio, et al. *Molecular cloning of the flavanone 3-beta-hydroxylase gene (FHT) from carnation (Dianthus caryophyllus) and analysis of stable and unstable FHT mutants*. Theoretical and Applied Genetics, 90(5):611-617, 1995.
L. Britsch, et al. *Molecular characterization of flavone-3'beta!-hydroxylases*. European Journal of Biochemistry, Oct. 1993, 217(2):745-754.

(Continued)

Primary Examiner—Ashwin Mehta
(74) Attorney, Agent, or Firm—Fish & Richardson P.C.

(57) ABSTRACT

A method of transforming a carnation (*Dianthus* L.) plant genome with a DNA molecule. The method comprises (a) preparing stem explants from carnation cuttings; (b) wounding the explants by microprojectile bombardment; (c) cocultivating the wounded explants with *Agrobacterium* comprising the DNA molecule under defined conditions of exposure to dark followed by light; (d) excising shoots from the cultivated wounded explants and removing the leaves from the shoots; and (e) culturing the leaves to obtain transgenic shoots transformed with the DNA molecule. Also disclosed are a rolC-transgenic carnation with improved agronomic traits and enhancement of flower fragrance by antisense suppression of the flavonoid gene fht.

14 Claims, 18 Drawing Sheets
(3 of 18 Drawing Sheet(s) Filed in Color)

OTHER PUBLICATIONS

Neal Gutterson. *Anthocyanin biosynthetic genes and their application to flower color modification through sense suppression.* Hortscience 30(5):964-966, 1995.

Amir Zuker, et al. *Wounding by bombardment yields highly efficient Agrobacterium-mediated transformation of carnation (Dianthus caryophyllus L.).* Molecular Breeding, 5(4):367-375, 1999.

Amir Zuker, et al. *Transformation of carnation by microprojectile bombarment.* Scientia Horticulturae (Amsterdam), 64(3):177-185, 1985.

Abed Watad, et al. *Adventitious shoot formation from carnation stem segments: A comparison of different culture procedures.* Scientia Horticulture (Amsterdam) 65(4):313-320, 1996.

A. Zuker, et al. *Genetic engineering for cut-flower improvement.* Biotechnology Advances 16(1):33-79, 1998.

A. Pellegrineschi, et al. *Improvement of ornamental characters and fragrance production in lemon-scented geranium through genetic transformation by agrobacterium rhizogenes.* Bio/Technology U.S., 12(1):64-68, 1994.

Zuker, et al. *Application of an intergrative system based on microprojectile bombardment and Agrobacterium tumefaciens to generate transgenic carnation plants with novel characteristics.* First International Congress On Plant Tissue and Cell Culture, Jerusalem, Israel, 1998.

XP-000921439 Ovadis, et al. *Generation of Transgenic Carnation Plants with Novel Characteristics by combining microprojectile bombardment with Agrobacterium tumefaciens transformation.* Plant Biotechnology and In Vitro Biology in the 21$^{st}$ Century, pp. 189-192, 1999.

XP-000921438 Zuker, et al. *A highly efficient method for carnation transformation.*

XP-002140940 Firoozabady, et al. *Efficient transformation and regeneration of carnation cultivars using Agrobacterium.*

XP-002140941 Zuker, et al. *Wounding by bombardment yields highly efficient Agrobacterium-mediated transformation of carnation (Dianthus caryophyllus L.).*

* cited by examiner

```
1    ATGGCTGAAG ACGACCTGTG TTCTCTCTTT TTCAAGCTCA AAGTGGAGGA TGTGACAAGC
61   AGCGATGAGC TAGCTAGACA CATGAAGAAC GCCTCAAATG AGCGTAAACC CTTGATCGAG
121  CCGGGTGAGA ATCAATCGAT GGATATTGAC GAAGAAGGAG GGTCGGTGGG CCACGGGCTG
181  CTGTACCTCT ACGTCGACTG CCCGACGATG ATGCTCTGCT TCTATGGAGG GTCCTTGCCT
241  TACAATTGGA TGCAAGGCGC ACTCCTCACC CGTACCAGCA TGATGTGACT
301  CTCGATGAGG TCAATAGAGG GCTCAGGCAA GCATCAGGTT TTTTCGGTTA CGCGGATCCT
361  ATGCGGAGCG CCTACTTCGC TGCATTTTCT TTCCCTGGGC GTGTCATCAA GCTGAATGAG
421  CAGATGGAGC TAACTTCGAC AAAGGGAAAG TGTCTGACAT TCGACCTCTA TGCCAGCACC
481  CAGCTTAGGT TCGAACCTGG TGAGTTGGTG AGGCATGGCG AGTGCAAGTT TGCAATCGGC
541  TAATGGTTAG TCGATGGGCT GACGAGTTTG ATGTCAGGAG AAGCTGAGTG TGTCACTTGT
601  TTCCCTTTAA GAAGTATTAA TGTAATAAAA ATCAAGATCT GGTTTAATAA CTGGATACTT
661  GATTTCATCG CGCTTTTTTT GAATAAATGT TTGTTGTCTT GACTTTAAGA TATCCTTTGA
721  AATTTGCGTT ATTCGTATTT CGCTTTTGGT TATTTCCAAA AGACTTTGCT CAGTAAGATC
781  AAACGTTTGT ATTTCTCCGG GCCACAATAT TTGACCTATA TGCACTGGCC CACGCGCCGC
841  AATAGATGAA AATTGCCAAA ATTAGCTATC GGTCTTCTGA AAAGAAGGGC CGACATGTTT
```

Fig. 6

901 TCATAGACCA TGCAAAGTCA TACTACCTGA AACTGATAAA TAACGACAAA GAAAGTAGCC
961 TATTTAAAAG TCGCTATAGC ATGAATT

Fig. 6 (cont.)

```
   1  ACTATATCTT AAATATTCAC AACATTATAA CATAAGCTTC AAAATAACAT
  51  TATTCCGATA TTTACGTAAT ATAATACGTA TCATATTAGG GTACATTCAT
 101  TTTATCAACT ACGACTGCAT ATTGTTAGAC AGTCTCATAT ATACGCATAA
 151  AAAATGGTCG CTGAAAAACC CAAAACGCTC ACTTCACTAG AAGGGGACGA
 201  TAAATTGAAC TCGAATTTTG TTAGGGACGA GGATGAACGT CCGAAAGTGG
 251  CGTATAATGA GTTTAGCAAT GATATTCCGG TGATATCTCT TGCTGGTATA
 301  GATGGTGAAA AAAGGGGTGA ATATGTCGG AAGATTGTTG AGGCGTGTGA
 351  AGATTGGGGG ATTTTTCAAG TGGTTGATCA CGGTGTTGGT GACGATCTTA
 401  TTGCTGATAT GACTCGGTTG GCTCGTGAAT TTTTCGCTCT CCCGGCAGAA
 451  GAGAAGCTCC GATTTGATAT GTCTGGTGGT AAAAGGGCG GTTTTATCGT
 501  GTCGAGTCAT CTTCAGGTTCAATCAACAGG GAGAAGTAGT GCAGGACTGG
 551  AGGGAAATCGTGACGTATTT CTCATACCCG ACGAACTCAA GGGACTACAC
 601  AAGATGGCCAGACAAACCAG AGGGTTGGAT AAAGGTCACA GAGGAATACA
 651   GCAACAAGTTAATGACCTTA GCATGTACAC TTTTAGGTGT ACTTTCTGAA
 701   GCCATGGGTTTAGAATTAGA GGCACTTACT AAAGCTTGTG TTGATATGGA
 751   CCAAAAGATTGTGGTTAATT ACTACCCTAA GTGCCCTCAA CCTGACCTTA
 801   CTTTAGGGCTCAAGAGGCAC ACCGACCCCG GACTATAAC CCTCCTCCTT
 851   CAGGACCAAGTCGGCGGTCT TCAGGCCACT CGTGACGGTG GTAAAACTTG
 901   GATTACCGTG CAGCCGGTTC CCGGTGCCTT CGTTGTTAAC CTTGGTGATC
 951   ATGGTCATGTTCGGCGAAAA ATGGCCAAAG ACCTTGAGAT CGCCCGTCAT
1001   AAGAGGCTTG CTAAAGAGGA AATGCCTTTT AAAGAGTTGG ACGAGGCCAA
1051   GTTTGAGTCC AAATCTATTG ACCAAATACT TGCTTAGATG GGCTTGGTTT
1101   GGTTTCATTA TATTAAATTT ATTATTATTA TTATTTATTG CATTTGATAT
1151   GATATGATTG GAAATAAAAG AGAGATTGTT TGTGATAATT TGTGTGATTA
1201   TTATATCACT AAGTTATGGC TTTAATTTGT GGTATGTTGG GAATTATATA
1251   TTTAGTTTTG TGTGAAGAAT ATATGATTTA AAGTTAAAAA AAAAAATGAT
1301   TTGTTATATGATTTACTTGT AAGGTTATAA GGTTATATTT ATTGTTCGAG
1351   TTTGCGTATA
```

Fig. 12

```
  1  CCAAGCCCAT CTAAGCAAGT ATTTGGTCAA TAGATTGGA CTCAAACTTG GCCTCGTCCA
 61  ACTCTTTAAA AGGCATTTCC TCTTTAGCAA GCCTCTTATG ACGGGCGATC TCAAGGTCTT
121  TGGCCATTTT TCGCCGAACA TGACCATGAT CACCAAGGTT AACAACGAAG GCACCGGGAA
181  CCGGCTGCAC GGTAATCCAA GTTTACCAC CGTCACGAGT GGCCTGAAGA CCGCCGACTT
241  GGTCCTGAAG GAGGAGGGT ATAGTCCCGG GGTCGGTGTG CCTCTTGAGC CCTAAAGTAA
301  GGTCAGGTTG AGGGCACTTA GGGTAGTAAT TAACCACAT CTTTGGTCC ATATCAACAC
361  AAGCTTTAGT AAGTGCCTCT AATTCTAAAC CCATGGCTTC AGAAAGTACA CCTAAAAGTG
421  TACATGCTAA GGTCATTAAC TTGTTGCTGT ATCCTCTGT GACCTTTATC CAACCCTCTG
481  GTTTGTCTGG CCATCTGTG TAGTCCCCTG AGTTCGTCGG GTATGAGAAA TACGTCACGA
541  TTTCCCTCCA GTCCTGCACT ACTTCTCCCT GTTGATTGAA CCTGAAGATG ACTCGACACG
601  ATAAACCGC CCTTTTTACC ACCAGACATA TCAAATCGGA GCTCTCTTC TGCCGGGAGA
661  GCGAAAAATT CACGAGCCAA CCGAGTCATA TCAGCAATAA GATCGTCACC AACACCGTGA
721  TCAACCACTT GAAAAATCCC CCAATCTTCA CACGCCTCAA CAATCTTCCG ACATATTCA
781  CCCCTTTTT CACCATCTAT ACCAGCAAGA GATATCACCG GAATATCATT GCTAAACTCA
841  TTATACGCCA CTTTCGGACG TTCATCCTCG TCCCTAACAA AATTCGAGTT CAATTTATCG
901  TCCCCTTCTA GTGAAGTGAG CGTTTGGG
```

Fig. 13

FIG. 14A 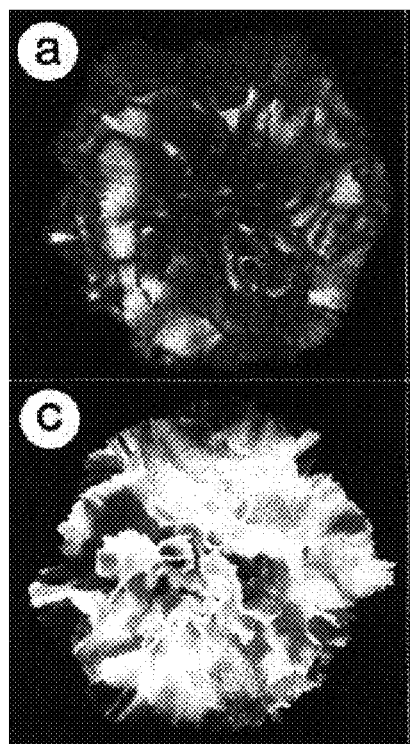 FIG. 14B 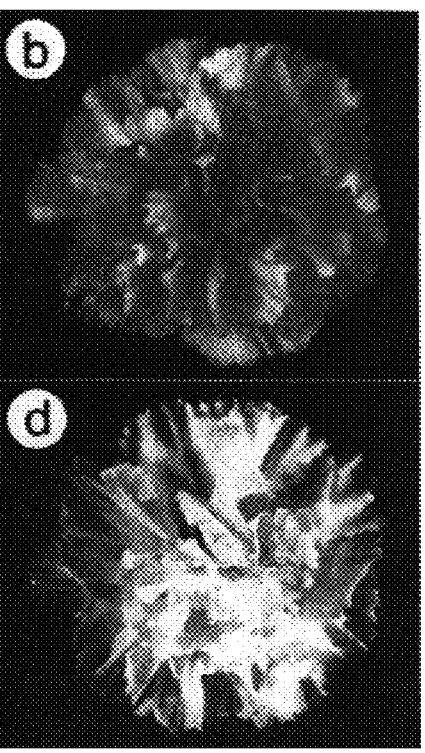
FIG. 14C 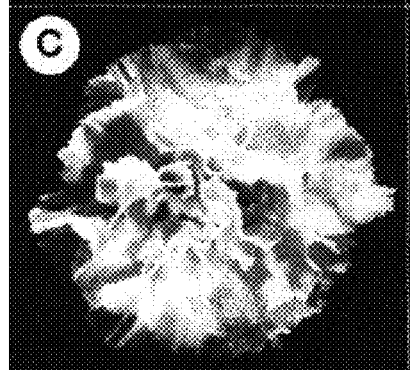 FIG. 14D 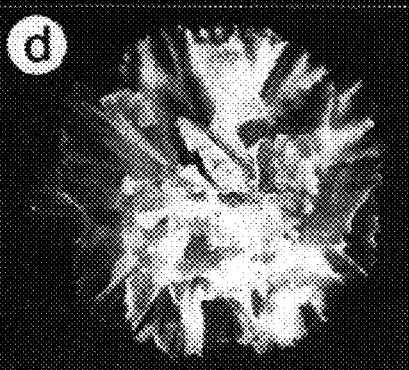
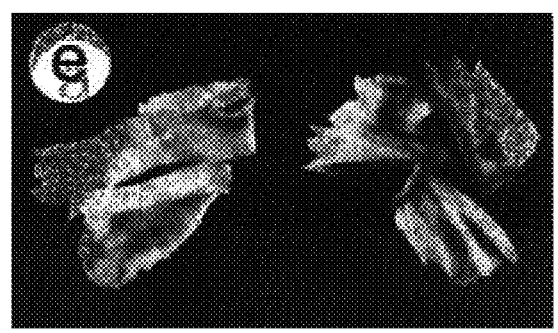
FIG. 14E

TRANSGENIC PLANTS AND METHOD FOR TRANSFORMING CARNATIONS

RELATED APPLICATIONS

This application is a U.S. National Phase application, which claims priority to International Application Ser. No. PCT/IL00/00110, filed on Feb. 22, 2000, and U.S. Provisional Application Ser. No. 60/121,239, filed on Feb. 22, 1999.

FIELD OF THE INVENTION

This invention relates to a method for transforming carnation plants and novel transgenic plants with improved traits.

BACKGROUND OF THE INVENTION

The following references may contribute to the understanding of the invention, and are referred to by number in the specification:
1. Zuker A, Tzfira T, Vainstein A: Genetic engineering for cut-flower improvement. Biotech Adv 16: 33–79 (1998)
2. van Altvorst A C, Rikesen T, Koehorst H, Dons J J M: Transgenic carnations obtained by Agrobacterium tumefaciens-mediated of leaf explants. Transgenic Res 4:105–113 (1995)
3. Zuker A, Chang P-F L, Ahroni A, Cheah K, Woodson W R, Bressan R A, Watad A A, Hasegawa P M, Vainstein A: Transformation of carnation by microprojectile bombardment. Sci Hort 64: 177–185 (1995)
4. Firoozabady E, Moy Y, Tucker W, Robinson K, Gutterson N: Efficient transformation and regeneration of carnation cultivars using Agrobacterium. Molecular Breeding 1: 283–293 (1995)
5. Lu C Y, Nugent G, Wardley-Richardson T, Chandler S F, Young R, Dalling M J: Agrobacterium-mediated transformation of carnation (Dianthus caryophyllus L.). Bio/Tech 9: 864–868 (1991)
6. Zuker, A., et al: Application of an integrative system based on microprojectile bombardment and Agrobacterium tumefaciens to generate transgenic carnation plants with novel characteristics. IX International Congress on Plant Tissue and Cell Culture, Jerusalem, Israel (1998)
7. Fladung, M., K. Grossmann, and M. R. Ahuja. 1997. Alterations in hormonal and developmental characteristics in transgenic Populus conditioned by the rolC gene from Agrobacterium rhizogenes. J. Plant Physiol. 150: 420–427
8. Scorza, R., T. W. Zimmerman, J. M. Cordts, K. J. Footen, and M. Ravelonandro. 1994. Horticultural characteristics of transgenic tobacco expressing rolC gene from Agrobacterium rhizogenes. J. Amer. Soc. Hort. Sci. 119:1091–1098
9. Nilsson, O. and O. Olsson. 1997. Getting to the root: the role of the Agrobacterium rhizogenes rol genes in the formation of hairy roots. Physiol. Plant. 100:463–473
10. Souq, F., P. Coutos-Thevenot, H. Yean, G. Delbard, Y Maziere, J. P. Barbe, and M. Boulay. 1986. Genetic transformation of roses, 2 examples: one on morphogenesis, the other on anthocyanin biosynthetic pathway. In: Morisot A, Ricci P (eds) Second International Symposium on Roses. Acta Hort. 424:381–388
11. Pelletier, M. K. & Shirley, B. W. Analysis of flavanone 3-hydroxylase in arabidopsis seedlings. Plant Physiol. 111, 339–345 (1996)
12. Ahroni A: Developing efficient regeneration and transformation methods for carnation and gypsophila. M. Sc. thesis (The Hebrew University of Jerusalem, Israel) (1996)
13. Tzfira, T., C. S. Jensen, W. Wang, A. Zuker, B. Vinocur, A. Altman, and A. Vainstein. 1997. Transgenic Populus tremula: a step-by-step protocol for its Agrobacterium-mediated transformation. Plant Mol. Biol. Rep. 15:219–235

The carnation (Dianthus L.), one of the world's major cut-flower crops, is the commercial leader in terms of number of stems sold worldwide. Different carnation types have been developed as a result of crossing and they can be divided into two main groups, standard (midi and mignon carnation) and spray (micro and diantini carnation); a minor group is formed by the pot carnations.

Market demand for flowers with improved traits—such as new colors, new shapes, better fragrance and longer vase life, drives breeders to create new and more attractive varieties every year. However, carnation is a vegetatively propagated crop and is very detrimentally affected by inbreeding. Hence, controlled breeding is rather complicated and limited due to the fact that selection of a desired trait in the siblings is performed on the genetic background of their two parents, and due to the very high genetic variability among offspring. Furthermore, crosses within and between related species is limited by a rather small available gene pool for new traits.

Biotechnological techniques such as genetic engineering could be a useful alternative/addition to currently used classical breeding methods for the production of novel plant varieties (1).

One of the prerequisites to generating transgenic plants is the availability of a regeneration system. For carnation, numerous procedures leading to efficient adventitious regeneration from a number of explants, including stem segments, leaves and petals, have been published (1). However, success in harnessing these regeneration systems to efficiently generate transgenes has been rather limited. The Agrobacterium-mediated transformation procedure described by van Altvorst et al. (2) and the microprojectile bombardment-mediated procedure (3) were both of relatively low efficiency.

A more recent, alternative transformation procedure was developed by DNAP Inc. (4). Although a high number of transgenes could be generated from the three varieties used, the procedure was extremely time-consuming and cumbersome because it relied on vitrified leaves as the primary explants and these can take 4 to 6 months of tissue culture to generate. The only efficient procedure reported to date, also used to generate transgenes with improved vase life, was developed by another biotech company, Calgene Pacific Ltd. (5). However extensive efforts by numerous groups to generate carnation transgenes with this experimental protocol have been unsuccessful. A preliminary report of an integrative system based on microprojectile bombardment and Agrobacterium-mediated transformation under a light regime and a two-step selection cycle has recently appeared (6).

New traits in cut flowers include not only yield improvement and resistance to insects or disease; they also consist of new colors and novel plant morphology. In fact, the latter are of great importance for the cut-flower market, where plant architecture and flower color are the main features determining consumer interest. Nevertheless, agronomic traits, such as performance, remain highly important for breeders and growers as extensively growing and better performing plants can lower the time and cost required for growth and breeding.

Among the different genes affecting plant morphology, e.g. homeotic, *Agrobacterium*, phytochrome and gibberellin genes, the *Agrobacterium rhizogenes* rol genes have been the most widely and successfully employed (7,8). Although its precise mode of action is still unknown (9), rolC has attracted the most attention through its expression in transgenic plant—either under its own promoter or under the control of a cauliflower mosaic virus (CaMV) 35S promoter, leading to a series of morphological alterations. These include reduced apical dominance, altered leaf morphology, reduced seed production, reduced internode length, male sterility, small flowers and early flowering, bushy and compact phenotype, and even stem fasciation.

Nevertheless, studies on the rolC gene and its effects on plant development have been performed mostly in model herbaceous plants, e.g. tobacco, potato, and tomato, or forest trees. rolC studies in cut flowers are rather limited—the only report being on a woody ornamental, rose, in the proceedings of a symposium (10). These transgenic rose plants (*Rosa* hybrida cv. Madame G. Delbard), expressing the rolC gene under its native promoter, exhibited an array of phenotypic alterations, most of which were highly disadvantageous horticulturally. They included a dramatically reduced root system, wrinkled leaves, high sensitivity to diseases and dying out of shoots.

With respect to color, anthocyanins, carotenoids and betalain are the main flower pigments, of which the most studied are the anthocyanins. The great interest in the latter, which derive from the general phenylpropanoid pathway, results from their wide distribution in many plants and microorganisms and their role in color determination. Furthermore, detailed biochemical and genetic analyses of anthocyanin production/accumulation has brought about the development of two main strategies for altering flower color: introducing a foreign gene(s) to allow new branching in the anthocyanin-biosynthesis pathway, and up/down-regulation of this pathway's native genes' expression.

Several genes from the anthocyanin biosynthetic pathway have been used to manipulate flower color in numerous plants. Chalcone synthase (chs), chalcone flavanone isomerase (chi) and flavanone 3-hydroxylase (fht) are the first three genes encoding the early, non-branched segment of the flavonoid biosynthetic pathway (FIG. 17). Although FHT is a key enzyme in this pathway (11) and its suppression, as opposed to that of CHS, should not block the production of the essential phytoalexins, isoflavonoids, it has never been harnessed for the genetic manipulation of flower color.

With respect to flower fragrance, mainly dominated by terpenoids, fatty acid derivatives and benzenoid compounds (phenylpropanoid derivatives), much less is known. To date, only a few genes involved in fragrance production have been characterized.

SUMMARY OF THE INVENTION

It is an object of the present invention to provide a method for transforming carnation plants.

It is a further object of the invention to provide transgenic carnation plants with desirable traits.

In one aspect of the invention, there is provided a method of transforming a carnation (*Dianthus* L.) plant genome with a DNA molecule comprising:

(a) preparing stem explants from carnation cuttings;
(b) wounding the explants by microprojectile bombardment;
(c) cocultivating the wounded explants with *Agrobacterium* comprising the DNA molecule under conditions of exposure to dark followed by light;
(d) excising shoots from the cultivated wounded explants and removing the leaves from the shoots; and
(e) culturing the leaves to obtain transgenic shoots transformed with the DNA molecule.

The method of the invention combines three experimental conditions to produce an efficient carnation transformation procedure: (1) the use of microprojectile bombardment to wound stem explants, (2) a specific dark/light regime to optimize transformation, and (3) an optimized two-cycle selection procedure.

Stem explants may be prepared from (stem) cuttings with e.g., four to ten fully mature leaves (not counting the apical leaves which were not fully expanded), harvested from greenhouse-grown plants and stored for up to 1 month at 4° C. The leaves and shoot apices may be removed and primary nodes (two to five) isolated.

Each bombardment typically consists of 50–200 µl of tungsten or gold particles in an aqueous suspension (10–20 mg/ml). Explants are generally placed on medium solidified with 1% agar and bombarded 1–2 times. Preferred particle acceleration parameters are: a bombardment pressure of 1300–2000 psi and a distance of 3–12 cm from the launching plate to the tissue.

Inoculated stem explants are cultured in an upright position for a period of time in the dark followed by a period of light. In a preferred embodiment, the explants are cocultivated for 2–4 days in the dark and then 1–4 days in the light. In a most preferred embodiment, the cultivation is carried out for 3 days in the dark followed by 2 days in the light.

For the first selection cycle during shoot regeneration from the stem explants, the basic medium was preferably supplemented with 0.04–1 mg/l NAA and 0.6–3 mg/l TDZ (SI-T1). After ca. 14–28 days, clusters of regenerated adventitious shoots are excised from the primary stem explants. Leaves from all of the shoots of each independent cluster are pulled off and cultured in medium supplemented with 0.04–1 mg/l NAA and 0.5–2 mg/l BAP (SI-B1) for adventitious shoot regeneration and selection of transgenes (second selection cycle). After 10 to 20 days, new adventitious transgenic shoots emerge from the leaf basal area.

In a second aspect of the invention, there is provided a transgenic carnation plant transformed with the *Agrobacterium rhizogenes* rolC gene.

In a preferred embodiment of this aspect of the invention, the rolC gene is under the control of a cauliflower mosaic virus (CaMV) 35S promoter.

In a further preferred embodiment of this aspect of the invention, the transgenic carnation plant is produced by the method of the first aspect of the invention.

In a most preferred embodiment of this aspect of the invention, the gene used to transform the carnation comprises the sequence shown in FIG. 6.

rolC-transgenic carnation plants (or "rolC transgenes") according to the invention generally exhibit increased axillary bud breakage and development when grown under standard commercial greenhouse conditions. rolC transgenes often generate up to 40% more stem cuttings per mother plant than controls. Stem cuttings from rolC transgenes usually exhibit better rooting ability, with up to five times higher root dry weight than controls. The improved rooting of rolC-transgenic cuttings is also apparent when commercial rooting powder is used. Analyses of plants during the flowering season reveal that rolC transgenes generally yield up to three times more flowering stems than control plants.

Improved rooting, for example, can lower the labor required to produce rooted stem cuttings. The importance of these traits is even more pronounced for commercial varieties that exhibit very low rooting percentages despite the application of rooting powder. With respect to the yield characteristics, e.g. number of stem cuttings and flowering stems per mother plant, these are obviously of major importance to carnation propagators and growers.

In a third aspect of the invention, there is provided a transgenic carnation plant wherein expression of the flavanone 3-hydroxylase (fht) gene is blocked.

In a preferred embodiment of this aspect of the invention, the expression of the fht gene is blocked by an antisense molecule.

In a most preferred embodiment of this aspect of the invention, the antisense molecule comprises the sequence of FIG. 13.

In a preferred embodiment, the transgenic carnation plant is produced by the method of the first aspect of the invention.

In this aspect of the invention, expression of a gene encoding flavanone 3-hydroxylase (fht), a key step in the anthocyanin pathway is blocked by antisense suppression in carnation. Transgenic carnation plants may exhibit flower color modifications ranging from attenuation to complete loss of their original color. Hence, carnation flowers in a variety of colors can be generated.

Approach to olfactory enhancement of natural fragrance (flower fragrance in particular) via diverting metabolic flow from anthocyanins to the production of benzoic acid derivatives (fragrance compounds) is demonstrated in carnation. In a preferred embodiment, transgenic carnation plants with a blocked flavonoid biosynthetic pathway (expression of the fht gene) may be generated using the above mentioned transformation procedure of the first aspect of the invention. Flowers of these carnation transgenes are much more fragrant than control plants.

In a fourth aspect of the invention, there is provided a method for controlling the fragrance of a plant comprising modulating gene expression in the anthocyanin-biosynthetic pathway of the plant.

In a preferred embodiment, the modulation comprises suppressing the expression of one or more genes in the pathway. An example of such a gene is the fht gene. In a most preferred embodiment, the suppression is by an antisense molecule.

DETAILED DESCRIPTION OF THE DRAWINGS

The file of this patent contains drawings executed in color. Copies of this patent with color drawings will be provided by the Patent and Trademark Office upon request and payment of the necessary fee.

In order to understand the invention and to see how it may be carried out in practice, a preferred embodiment will now be described, by way of non-limiting example only, with reference to the accompanying drawings, in which:

FIG. 1 shows the effect of wounding and cocultivation on the efficiency of transient transformation of cv. White Sim stem explants. Explants were wounded by bombardment (+) or just poking/scratching and cocultivated with EHA105/pKIWI105 for 5 days under constant light or in the dark. GUS expression is presented as the number of blue spots per stem explant. S. E. of the mean (p=0.05) is indicated (n=5).

FIG. 2 illustrates transient transformation frequencies of different carnation cultivars. Following bombardment, stem explants were cocultivated with EHA105/pKIWI105 for 3 days in the dark and 2 days under constant light as described in Materials and Methods. GUS expression is presented as the number of blue spots per stem explant. S. E. of the mean (p=0.05) is indicated (n=5).

FIGS. 3A–H illustrate transformation and regeneration of transgenic carnation plants. (A) GUS expression on the cut surface of a stem explant 14 days after inoculation. (B) Shoot regeneration from a stem explant. (C) The chimeric pattern of GUS expression following the first selection cycle. (D) Second selection cycle of adventitious shoots. Shoots developed from the leaf area which showed resistance to kanamycin, as reflected by its green color. The white, non-resistant area remained non-regenerative (arrow). (E,F) Solid, non-chimeric GUS expression in adventitious shoots regenerated from leaves following the second selection cycle. (G) Transgenic flowers. (H) GUS-expressing seedlings ($T_1$) obtained from crosses of transgenic cv. White Sim with non-transformed (b.l. 13261/2/3) male plants.

FIG. 4 shows southern blot analysis of DNA from four independent transgenic (1–4) and one non-transformed (C) cv. White Sim carnation plants. Total DNA (10 µg) was digested with EcoRI (left) or HindIII (right) and hybridized with a uidA probe. (P) Plasmid pCGN7001 digested with EcoRI.

FIG. 5 shows a Southern blot of PCR analysis of offspring ($T_1$). DNA for nptII PCR analyses was prepared from GUS-expressing kanamycin-resistant $T_1$ progeny plants ($T_0$ cv. White Sim x b.l. 13261); $T_0$ plants; control, non-transformed plants (C); and plasmid pCGN7001 (P). Following nptII-PCR amplification and gel electrophoresis, the products were hybridized with nptII probe.

FIG. 6 shows the DNA sequence of the *Agrobacterium rhizogenes* rolC gene (SEQ ID NO:1).

FIG. 7 illustrates a schematic illustration of a typical carnation stem cutting. Each cutting is composed of three to five internodes (I to V). Each node carries two opposite leaves and two axillary buds which can develop into side shoots. The developmental stage of these side shoots was graded according to the number of open pairs of leaves on them (0, 1 or 2).

FIGS. 8A and 8B show a molecular analysis of three independent rolC-transgenic (R-1, R-2 and R-3) and control uidA-transgenic (C) cv. White Sim carnation plants. (A) Southern blot analysis of HindIII-digested total DNA. (B) Northern blot analysis of total RNA. Both blots were hybridized with rolC probe.

FIG. 9 illustrates a distribution of stem-cutting types in rolC-transgenic (R-1, R-2 and R-3) and control (C) carnation plants. Stem cuttings were classified as III, IV or V according to the number of internodes they carried, as depicted in FIG. 7.

FIG. 10 illustrates adventitious root dry weight and rooting percentages in stem cuttings of rolC-transgenic lines (R-1, R-2 and R-3) and control (C) carnation plants after 30 days on rooting tables, as detailed in Materials and Methods of Example II. Bars represent an average of 15 stem cuttings per line; SE of the mean is indicated. The numbers above the bars represent the rooting percentages, i.e. percent of cuttings developing roots out of total number of cuttings.

FIGS. 11a, 11b, 11c and 11d show morphological alterations in rolC-transgenic carnation plants: (11a) Rooted stem cuttings of control (left) and rolC-transgenic line R-1 (right). (11b) Flowers of rolC-transgenic line R-2 (top) and control (bottom) plants. (11c) Adventitious root formation in line R-1 (left) and control (right) plants. (11d) Flowering stems of rolC-transgenic lines and control plants (from left to right: R-1, R-2, R-3, control).

FIG. 12 shows the cDNA sequece of fht from carnation (SEQ ID NO:2).

FIG. 13 shows the sequence of the antisense fragment to the fht cDNA (SEQ ID NO:3).

FIGS. 14a, 14b, 14c, 14d and 14e show flower color modification of anti-fht transgenic carnation. Cv. Eilat was transformed with fht cDNA cloned into a binary plasmid in antisense orientation 3' to 35S CaMV. a. Flower from control, non-transformed cv. Eilat. b–d. Flowers from cv. Eilat transformed with antisense fht (transgenic lines FHT-33, FHT-11, FHT-14, respectively). e. Complementation of FHT suppression in the petals of line FHT-11, by feeding with dihydroquercetin in 5% methanol (right). On the left, petals incubated in 5% methanol.

Figure 15:
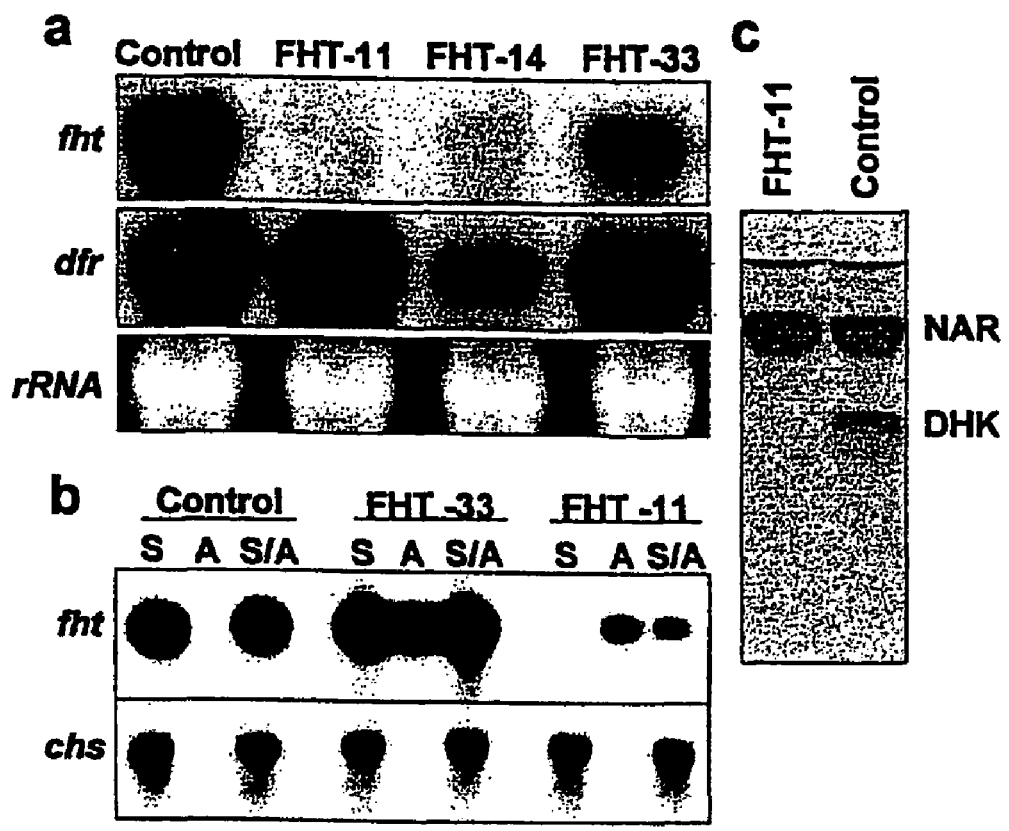

FIG. 15 illustrates molecular and biochemical characterization of anti-fht transgenic plants a. Northern blot analysis of fht transcript levels in petals of anti-fht transgenic FHT-11, FHT-14 and FHT-33 and control, cv. Eilat. For comparison, analysis of dfr transcript is presented b. Analysis of fht sense and antisense transcript accumulation in petals of control, cv. Eilat and anti-fht transgenic FHT-11 and FHT-33. Strand-specific primers were used to reverse-transcribe sense (S), antisense (A) and both (S/A) transcripts, followed by PCR amplification and Southern analysis. chs analysis was used as a control. c. FHT enzyme activity in petal extracts of control, cv. Eilat and anti-fht transgenic FHT-11 plants. [$^{14}$C]naringenin (NAR) was used as a substrate for the reaction, and the FHT enzyme activity product, dihydrokaempferol (DHK), was analyzed by TLC followed by autoradiography.

Figure 16:
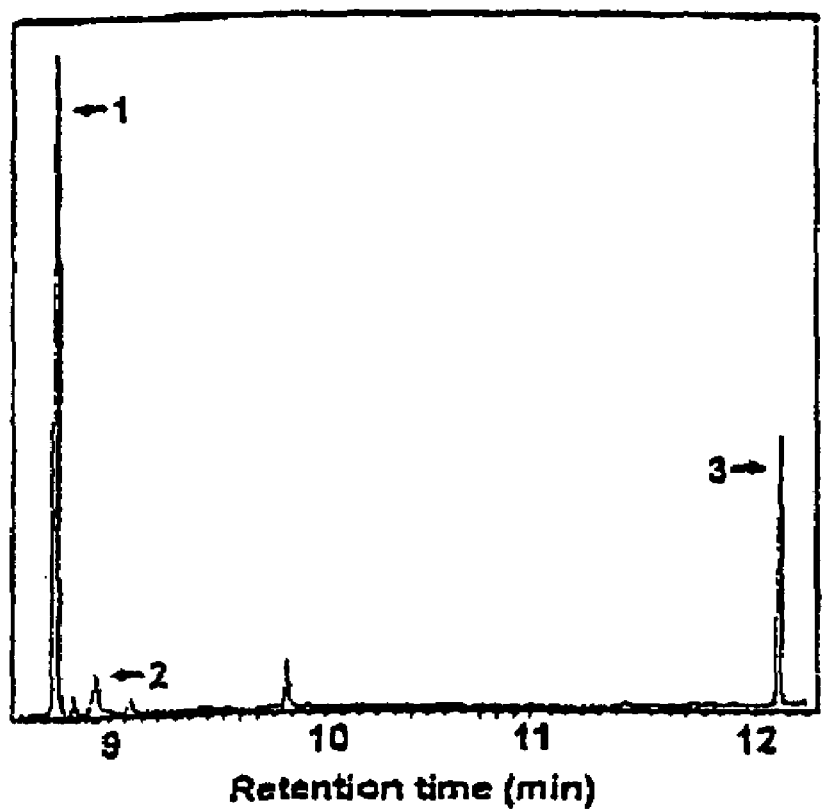
Figure 17:
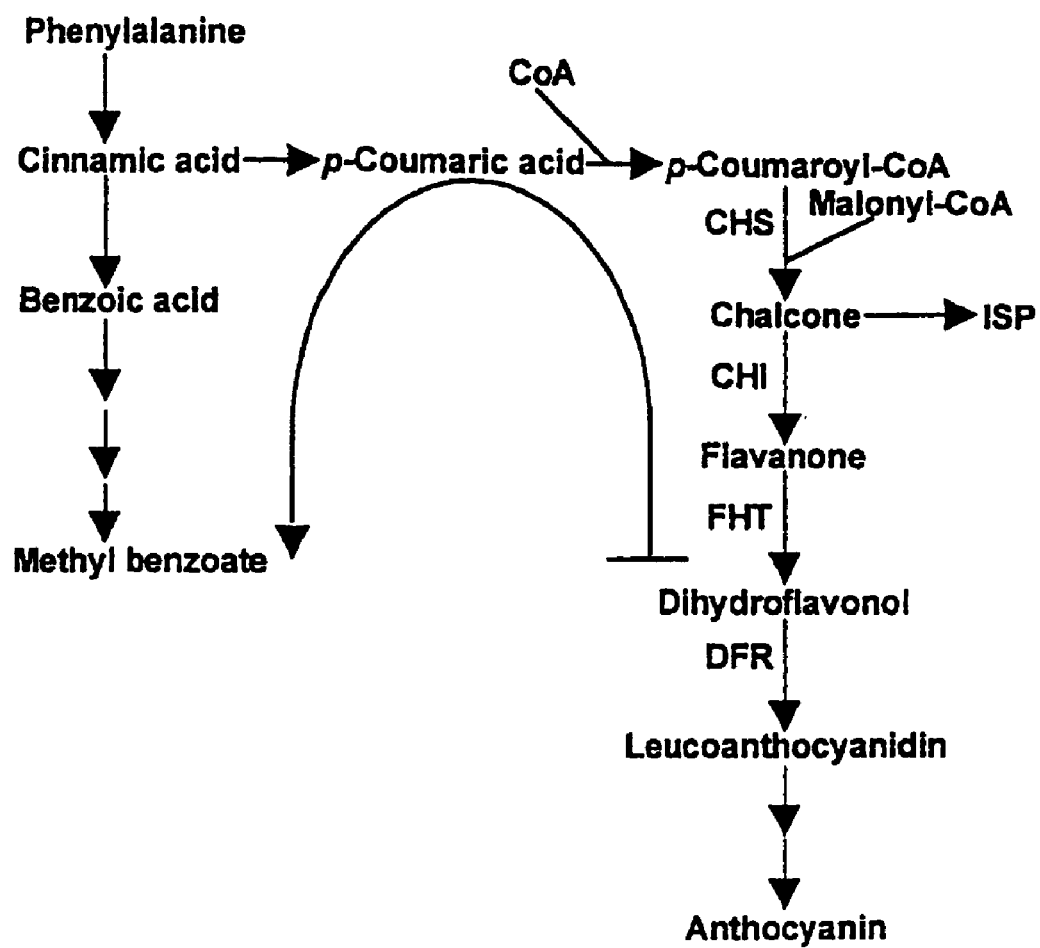

FIG. 16 shows gas chromatography-mass spectroscopy (GC-MS) headspace analysis of volatile compounds, emitted from detached flowers of anti-fht transgenic FHT-11 plants. A representative GC chromatogram is presented. 1, methylbenzoate; 2, hexanoic acid; 3, trans-caryophyllene; and FIG. 17 is a schematic presentation of anthocyanin and benzoic-acid-derivative biosynthesis, originating from the general phenylpropanoid pathway. The diversion of metabolic flow in the direction of benzoic-acid-derivative production, as a result of FHT suppression, is depicted. Enzymes are indicated as follows: chalcone synthase (CHS); chalcone flavanone isomerase (CHI); flavanone 3-hydroxylase (FHT); dihydroflavonol 4-reductase (DFR). ISP, isosalipurposide.

DETAILED DESCRIPTION OF PREFERRED EMBODIMENTS

I. Method of Carnation Transformation

A. Materials and Methods

1. Plant Material

Carnation plants were grown under standard greenhouse conditions. The experiments described below were carried out using the carnation species Dianthus caryophyllus L. However, it is to be understood that this is only an exemplary species, and this aspect of the invention applies to all species of the Dianthus genus. Cultivars White Sim, Eilat, Darling, Visa and Lior were grown at the Faculty of Agriculture (The Hebrew University of Jerusalem, Israel) and Shemi Ltd. (Shdema, Israel), and cultivar Desio was received from Mizpor Ltd. (Tquma, Israel). Cultivars White Sim, Desio and Visa belong to the standard category while cv. Eilat, Darling and Lior belong to the spray category. Stem cuttings with six or eight fully mature leaves (not counting the apical leaves which were not fully expanded), harvested from greenhouse-grown plants and stored for up to 1 month at 4° C., were used to prepare stem explants.

2. Media Composition and Tissue-Culture Conditions

Murashige and Skoog (Murashige T, Skoog F: A revised medium for rapid growth and bioassays with tobacco tissue culture. (1962) Physiol Plant 15: 473–497) basal medium (MS) with sucrose (30 g/l) and solidified with agar (8 g/l) (basic medium), was supplemented with growth regulators and antibiotics for cocultivation with Agrobacterium, regeneration and selection of adventitious shoots, and elongation and rooting of transgenic plants. All media were adjusted to pH 5.8 prior to autoclaving (121° C. for 20 min). For cocultivation with Agrobacterium, the basic medium was supplemented with 5 mg/l α-naphthalene acetic acid (NAA) and 100 μM acetosyringone (cocultivation medium). For shoot regeneration and two-step selection of transformants, the basic medium was supplemented with 0.1 mg/l NAA and 1 mg/l 1-phenyl-3(1,2,3-thiadiazol-5-yl)-urea (TDZ) (SI-T1, first selection cycle), or with 0.1 mg/l NAA and 1 mg/l 6-benzylaminopurine (BAP) (SI-B1, second selection cycle). Both media were also supplemented with 300 mg/l carbenicillin and, unless otherwise stated, 100 mg/l kanamycin. Elongation and rooting of transgenic shoots, following the second selection cycle, were performed on the basic medium containing 0.1 mg/l NAA, 0.1 mg/l gibberellic acid (GA), 200 mg/l carbenicillin and 100 mg/l kanamycin. All cultures were maintained in a growth room at 25±1° C. under a 16-h photoperiod using cool white light (60 μmol m$^{-2}$s$^{-1}$) unless otherwise indicated.

3. Bacterial Strains

Agrobacterium tumefaciens strains AGLO (Lazo G, Stein P, Ludwig R. A DNA transformation-competent Arabidopsis genomic library in Agrobacterium. (1991) Bio/Tech 9: 963–967) and EHA105 (Hood E, Gelvin S, Melchers L, Hoekema A: New Agrobacterium helper plasmids for gene transfer to plants. (1993) Trans Res 2: 208–218.) carrying the binary plasmids pCGN7001 (Comai L, Moran P, Maslyar D: Novel and useful properties of a chimeric plant promoter combining CaMV 35S and MAS elements. (1990) Plant Mol Biol 15: 373–381) and pKIWI105 (Janssen B, Gardner R: Localized transient expression of GUS in leaf disks following cocultivation with Agrobacterium. (1989) Plant Mol Biol 14: 61–72), respectively, were used for transient and stable transformation of carnation, respectively. Both plasmids carried the uidA gene coding for β-glucuronidase (GUS) (Stomp A M: Histochemical localization of β-glucuronidase. In: Gallagher S R (ed) GUS Protocols: Using the GUS Gene as a Reporter of Gene Expression, pp. 103–113. Academic Press, San Diego (1992)) driven by either a cauliflower mosaic virus (CaMV) 35S promoter (pKIWI105) or a mannopine synthetase (MAS) promoter (pCGN7001) (Comai L, et al), and the nptII gene coding for neomycin phosphotransferase II (NP-TII) (Beck E, Ludwig G, Auerswald E A, Reiss R, Schaller H: Nucleotide sequence and exact location of the neomycin phosphotransferase gene from transposon Tn5. (1982) Gene 19: 227–336) driven by either a nopaline synthase (NOS) promoter (pKIWI105) or the CaMV 35S promoter (pCGN7001).

The GUS-encoding gene is not expressed in *Agrobacterium* cells carrying pKIWI105 due to the lack of a bacterial ribosome-binding site, making this plasmid suitable for transient transformation studies (Janssen, et al). Digestion of pCGN7001 with EcoRI releases a 3.8-kb fragment containing uidA and part of nptII, whereas HindIII is a unique restriction site within the T-DNA fragment (Comai, et al).

Bacteria from a single colony were grown at 28° C. for ca. 20 hours in liquid LB medium (10 g/l bacto-tryptone, 5 g/l bacto-yeast extract, 5 g/l NaCl, 2 g/l glucose, pH 7.5) on a rotary shaker (250 rpm). The medium was supplemented with 100 μM acetosyringone, 50 mg/l rifampicin, and 25 mg/l gentamycin or 50 mg/l kanamycin for pCGN7001 or pKIWI105, respectively. Bacteria ($OD_{550}$=0.5) was harvested by centrifugation at 10000 g for 2 min; the pellet was resuspended in liquid cocultivation medium ($OD_{550}$ 0.5 or 1.0), and the suspension was used for inoculation.

4. Microprojectile Bombardment

Leaves and shoot apices were removed from sterilized cuttings and the three primary nodes were wounded prior to inoculation in a Biolistics PDS 1000/He system using tungsten M-25, 1.7 μm in diameter (Bio-Rad, Richmond, Calif., USA). Explants placed on MS basal medium solidified with 1% agar (30 explants per petri dish) were bombarded twice. Each bombardment consisted of 100 μl of tungsten particles in an aqueous suspension (15 mg/ml). The particles were finely dispersed with ultrasonic cleaner (Sonicor Instrument Corporation, Copiague, N.Y., USA) before bombardment. Particle acceleration parameters were: a bombardment pressure of 1500 psi and a distance of 9 cm from the launching plate to the tissue.

5. Optimization of Transient Transformation

Stem explants with or without prior wounding by microprojectile bombardment were immersed for 10 min in a bacterial (*A. tumefaciens* EHA105/pKIWI105) suspension ($OD_{550}$=1). Inoculated stem explants were then blotted dry and cultured in an upright position on the cocultivation medium under various light regimes for a period of up to 5 days. Following cocultivation, stem explants were histochemically evaluated for transient GUS expression by counting the number of GUS-expressing stem explants, as well as the number of blue spots per explant, under a stereo-microscope.

6. Transformation and Regeneration of Transgenic Plants

Following bombardment-mediated wounding, stem explants were inoculated with bacterial (AGLO/pCGN7001) suspension ($OD_{550}$=0.5). During cocultivation and all consecutive steps, explants were cultured in an upright position. After 5 days of culture on the cocultivation medium (3 days in the dark followed by 2 days in light), three primary nodes were sectioned into ca. 3-mm slices and transferred to SI-T1 medium for shoot regeneration and the first selection cycle. It should be noted that apical meristem breakage was considered undesirable. Hence, to prevent the development of non-transformed axillary shoots, all identifiable shoot apices were removed from the stem explants prior to inoculation with bacteria.

After 10 days of culture, the explants were cleaned again, if needed, of the occasionally developing shoots, cross-sectioned into two halves, and transferred to fresh SI-T1 medium. After ca. 2 additional weeks, clusters of regenerated adventitious shoots were excised from the primary stem explants. Leaves from all of the shoots of each independent cluster were pulled off and cultured on SI-B1 medium for adventitious shoot regeneration and selection of transgenes (second selection cycle).

After 10 to 12 days, new adventitious shoots emerged from the leaf basal area. These shoots were transferred to elongation and then rooting media and evaluated as to their transgenic nature. Following hardening (Vainstein A, Fisher M, Ziv M: *Shoot regeneration from petals as a basis for genetic variation and transformation*. (1992) Acta Hortic 314: 39–45), transgenic plants were transferred to the greenhouse where they developed and flowered normally. Since cv. White Sim, like most commercial carnation varieties, is male-sterile and can only be out-crossed, $T_0$ White Sim plants were crossed with wild-type (non-transformed) red (b.1. 13261), yellow (b.1. 13262) or white (b.1. 13263) male plants to generate $T_1$ progeny. All crosses were carried out in the fall/winter and seeds were collected and sown in the summer. Seedlings were evaluated for GUS expression and were subjected to uidA and nptII PCR analysis. All transformation experiments were repeated at least five times.

7. Evaluation of Transformants a. GUS Expression

A histochemical assay of GUS activity was performed according to Stomp. Tissue samples were incubated for a few hours to overnight at 37° C. in a 0.1% (w/v) X-Gluc (5-bromo-4-chloro-3-indolyl β-D-glucuronic acid sodium salt, Biosynth Inc., Staad, Switzerland) solution containing 0.1 M sodium phosphate buffer (pH 7.0), 10 mM EDTA, and 0.1% (w/v) Triton X-100. When necessary, green tissues were bleached, after staining, by immersion in 50% (v/v) EtOH for a few hours, followed by several washes with 70% EtOH. It should be noted that no background GUS activity was detectable in any of the analyzed—intact or wounded—tissues of control plants.

b. Polymerase Chain Reaction (PCR) Analysis

DNA extraction, primers for uidA, and PCR conditions were as previously described (Tzfira T, Jensen C S, Wangxia W, Zuker A, Altman A, Vainstein A: Transgenic *Populus*: a step-by-step protocol for its *Agrobacterium*-mediated transformation. (1997) Plant Mol Biol Rep 15:219–235). The primers for nptII amplification were 5'-GAGGCTATTCG-GCTATGACT-3' (SEQ ID NO:4) and 5'-AATCTCGT-GATGGCAGGTTG-3' (SEQ ID NO:5). The predicted sizes of the amplified DNA fragments were 0.53 kb and 0.8 kb for uidA and nptII, respectively. Amplified DNA was electrophoresed on a 1.5% (w/v) agarose gel, using Tris-borate buffer (1.3 M Tris, 0.7 M boric acid and 24.5 mM EDTA, pH 8.4). Gels were stained with ethidium bromide, photographed under ultraviolet light, and analyzed by Southern blotting.

c. Southern Blot Analysis

DNA was extracted from leaves by the CTAB (cetyltrimethylammonium bromide) procedure described previously (Tzuri G, Hillel J, Lavi U, Haberfeld A, Vainstein A: *DNA fingerprints of ornamental plants*. (1991) Plant Sci 76: 91–97). DNA (10 μg) was digested with HindIII or EcoRI and electrophoresed in 1% (w/v) agarose gels. DNA was transferred to a nylon membrane (Hybond N+, Amersham) by capillary blotting as previously described (Maniatis T, Fritsch E F, Sambrook J: *Molecular Cloning. A Laboratory Manual*. (1982) Cold Spring Harbor Laboratory Press, Cold Spring Harbor). PstI fragments of 2.6 kb and 1.9 kb from the binary plasmid p35SGUSINT Vancanneyt G, Schmidt R, O'Connor-Sanchez A, Willmitzer L, Rocha-Sosa M: *Construction of an intron-containing marker gene: splicing of the intron in transgenic plants and its use in monitoring early events in Agrobacterium-mediated plant transformation.* (1990) Mol Gen Genet 220: 245–250) served as probes for uidA and nptII, respectively. The probes were $^{32}$P-labeled by random priming (Feinberg A P, Vogelstein B: *A technique for radiolabelling DNA restriction endonuclease fragments to high specific activity.* (1984) Anal Biochem 137: 266–267), denatured and added to the hybridization mixture.

Pre-hybridization and hybridization were performed as previously described (Ben-Meir H, Vainstein A: *Assessment of genetic relatedness in roses by DNA fingerprint analysis.* (1994) Sci Hortic 58: 115–121) at 65° C. for 3 h and 18 h, respectively. Post-hybridization washes consisted of two high-stringency washes in 0.45 M NaCl, 0.045 mM sodium citrate, 0.1% (w/v) SDS, 65° C., for 20 min each, followed by one wash in 0.15 M Nacl, 0.015 mM sodium citrate, 0.1% SDS, 65° C., for 20 min. The blots were exposed to an imaging plate (Fujix Bas 1000, Fuji, Japan) for 2–7 h. The plate was then read in an imaging plate reader (Fujix Bio Imaging Analyzer Bas 1000). Two washes of 0.6 M NaCl, 0.06 mM sodium citrate, 0.1% SDS, 65° C., for 20 min each, were added prior to the three post-hybridization washes when Southern blots were performed with the PCR products.

B. Results

1. Optimization of Transient Transformation uidA (GUS) reporter gene expression was used to monitor early transformation events in carnation stem explants. Preliminary experiments testing different wounding methods (vortexing of stem explants in the presence of glass beads, sand or carborundum particles, or poking and scratching with a needle or scalpel) yielded neither efficient nor reliable transient transformation following inoculation (with or without vacuum infiltration) with *Agrobacterium* (12).

Figure 1:
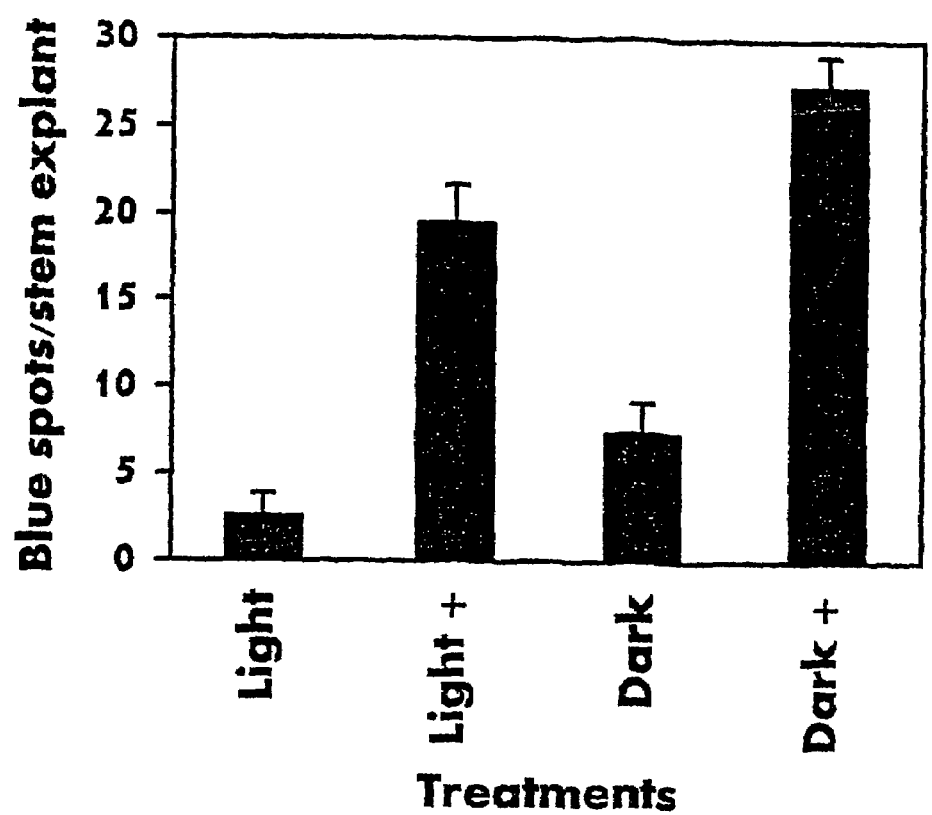

In contrast, when explants were wounded by microprojectile bombardment, efficient and highly reproducible transient transformation was obtained, based on both the percentage of GUS-expressing inoculated explants and the frequency of transformation events per explant. Following a 5-day cocultivation with EHA105/pKIWI105 under constant light, 90% of the cv. White Sim stem explants expressed GUS when they had been wounded by bombardment, as compared to only 20% GUS-expressing explants when wounding had been effected by poking or scratching. The transient frequency events (the number of blue spots per explant) increased 7.5-fold when bombardment-mediated wounding of explants was employed (FIG. 1). It should be noted that cocultivation with *Agrobacterium* for less than 5 days yielded lower transformation efficiencies (data not shown).

Different light conditions during cocultivation also strongly affected the efficiency of transient transformation. An almost threefold increase in the number of transformation events per explant was obtained when non-bombarded explants were cocultivated in the dark instead of under constant light (FIG. 1). When bombardment-mediated wounding was combined with etiolation during cocultivation, the frequency of transformation events per explant increased to over 10-fold that of explants wounded by other means and cocultivated in the light (FIG. 1). However, the relatively long etiolation period led to decreased regeneration from stem explants in both *Agrobacterium*-inoculated and noninoculated (control) stem explants.

To restore these explants' high regeneration potential while preserving the positive effect of etiolation on transformation, the effect of different dark/light regimes on transient GUS transformation and regeneration efficiencies was assessed. When stem explants were cocultivated with *Agrobacterium* for 3 days in the dark then 2 days in the light, the high regeneration efficiency of the explants was restored, reaching the level of those cocultivated for 5 days in the light. Moreover, transformation efficiency was not affected relative to explants cocultivated for 5 days in the dark (cv. White Sim in FIGS. 1 and 2).

Figure 2:
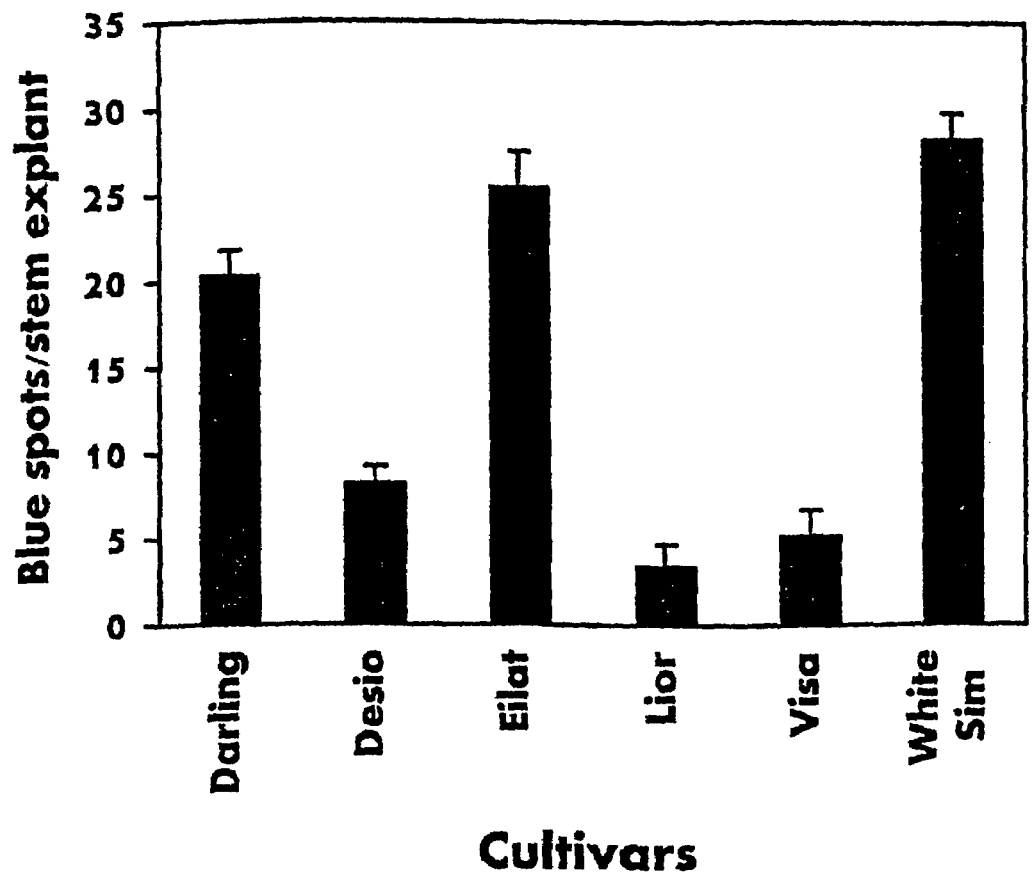

To assess the suitability of the combined wounding and dark/light regime to other carnation cultivars, transient transformation frequencies in five varieties representing both standard and spray categories were analyzed. All five were susceptible to transformation with EHA105/pKIWI105 under the aforementioned conditions. For all cultivars, 80–90% of the inoculated explants expressed GUS, albeit with some variation in the frequency of transformation events per stem explant (FIG. 2). Further experiments were performed using this combination of wounding and inoculation/cocultivation conditions.

2. Stable Transformation and Regeneration of Transgenic Plants

To improve the effectiveness of kanamycin for transgene selection, stable transformation of cv. White Sim was performed with pCGN7001 which carries 35S-driven nptII, rather than the NOS-driven nptII of pKIWI105 used in the transient transformation experiments. When inoculation was performed with a high concentration of bacteria ($OD_{550} \geq 1$), their extensive growth prevented the establishment of aseptic cultures, even at high concentrations of antibiotics, and negatively affected adventitious shoot regeneration. Inoculation of explants with bacteria at an $OD_{550}$ of 0.5 was optimal, allowing controlled bacterial growth with no adverse effect on the further tissue culture and regeneration of plantlets following transfer to the regeneration/selection SI-T1 medium.

After ca. 1 month in culture following inoculation, adventitious shoot clusters, regenerated directly from sectioned stem explants, were easily scorable (FIG. 3). Interestingly, while all three internodes showed high regeneration ability in aseptic tissue culture, only the two top internodes retained this potential following inoculation and selection. Histochemical evaluation of regenerated clusters revealed a chimeric GUS expression pattern in most of the adventitious shoots (FIG. 3), despite high selection pressure (100 mg/l kanamycin) during regeneration; only 1 to 3% of all regenerated shoots expressed GUS in and throughout all analyzed tissues. Since the application of a higher kanamycin concentration (120 and 150 mg/l) in the first selection cycle led to reduced shoot regeneration while transformed plants remained mostly chimeric in nature (data not shown), a second selection cycle was performed to eliminate the chimeric plants.

Figure 3A:
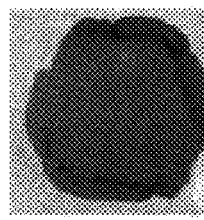
Figure 3B:
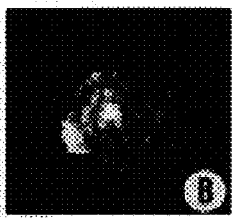
Figure 3C:
Figure 3D:

Leaves originating from individual clusters were cultured, separately for each cluster, on SI-B1 medium to eliminate the possibility of generating transgenes representing a single transformation event. After ca. 2 weeks of the second-selection cycle, two-thirds of the independent clusters selected on 100 mg/l kanamycin yielded scorable shoots (Table 1). These adventitious shoots regenerated directly from the basal part of the leaves, and only from an area which remained green under kanamycin selection (FIG. 3D).

TABLE 1

Efficiency of selection of transformed carnation plants. Stem explants of cv. White Sim were transformed with *Agrobacterium tumefaciens* AGLO/pCGN7001 as described in the experimental protocol.

| First selection cycle | | Second selection cycle (100 mg/l kanamycin) | |
|---|---|---|---|
| | | No. of clusters | |
| Kanamycin (mg/l) | No. of selected clusters* | generating shoots** | No. of GUS-expressing shoots*** |
| 80 | 92 ± 35 | 29 ± 1 (32) | 17 ± 1 (59) |
| 90 | 65 ± 4 | 25 ± 2 (38) | 20 ± 1 (80) |
| 100 | 32 ± 4 | 21 ± 1 (66) | 19 ± 1 (90) |

*The number of harvested independent shoot clusters regenerated from a total of 100 stem explants, following the first selection cycle.
**The number of independent clusters that generated shoots from leaves following the second selection cycle. The numbers in brackets represent percentages of independent clusters generating shoots from leaves following the second selection cycle out of the total number of independent clusters selected in the first selection cycle.
***The number of independent clusters generating GUS-positive shoots from leaves following the second selection cycle. The numbers in brackets represent percentages of independent clusters generating GUS-positive shoots from leaves out of the total number of independent clusters generating shoots following the second selection cycle.

Figure 3E:
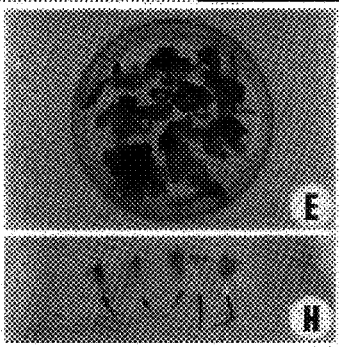
Figure 3H:
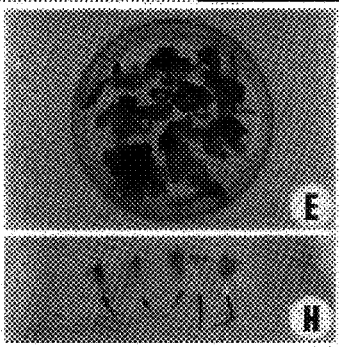
Figure 3F:
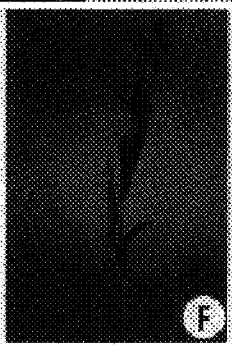

In almost all of these shoots, histochemical assay revealed GUS expression in all organs and throughout the tissues, with no observable chimerism (Table 1, FIG. 3E, 3F). To assess the overall efficiency of the two cycles of selection, only one GUS-expressing shoot per individual cluster was counted, even though 5–20 GUS-expressing shoots were usually generated from leaves of each cluster. Based on this consideration, which allows an estimation of independent transformation events, the overall yield of the procedure was 19 GUS-expressing shoots generated per 100 *Agrobacterium*-inoculated stem explants.

The possibility of further increasing the overall yield by lowering the selection pressure during the first selection cycle was assessed (Table 1). Following cocultivation, stem explants were cultured on SI-T1 medium containing 80 and 90 mg/l kanamycin instead of 100 mg/l. The lowest kanamycin concentration yielded ca. three times more and 90 mg/l kanamycin ca. two times more shoot clusters relative to the number regenerated on 100 mg/l kanamycin. However, only ca. one-third of the clusters generated at both 80 and 90 mg/l kanamycin yielded adventitious shoots from leaves following the second selection cycle. Thus, while the overall number of independent GUS-expressing shoots was essentially the same for the three levels of kanamycin analyzed, 100 mg/l was considered optimal because it almost completely prevented the generation of escapees (Table 1).

Figure 3G:

Forty randomly selected independent, kanamycin-resistant, GUS-expressing $T_0$ cv. White Sim plants exhibited a normal phenotype when, following hardening, they were grown to flowering in the greenhouse. Progeny generated from an outcross of the $T_0$ White Sim lines also expressed GUS and flowered normally (FIG. 3G, 3H).

Figure 4:
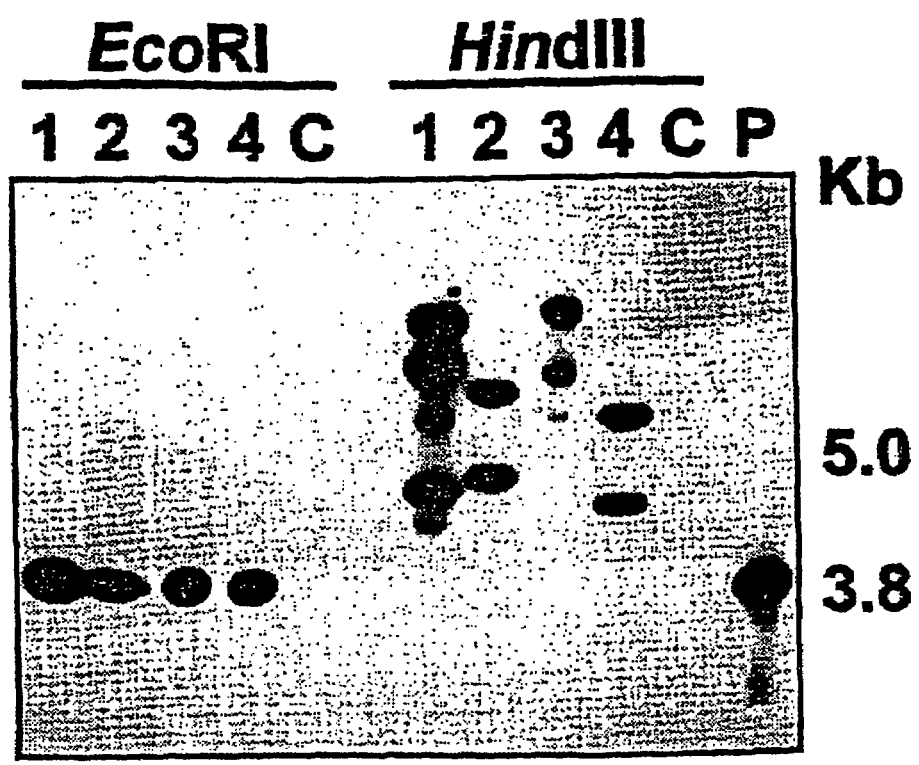
Figure 5:
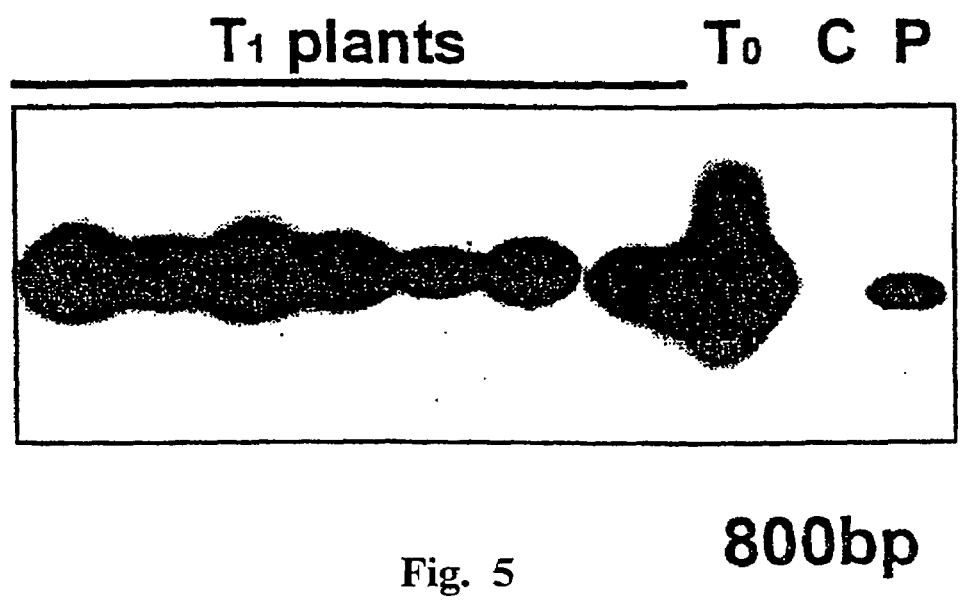

To further confirm the transgenic nature of the generated kanamycin-resistant GUS-expressing plants, Southern blot analysis was performed. Hybridization of EcoRI-digested genomic DNA from $T_0$ lines with uidA probe yielded the expected 3.8 kb fragment (FIG. 4, lanes 1–4); this fragment was not detectable in the non-transformed control line (FIG. 4, lane C). Two to four fragments of different sizes were revealed following digestion of $T_0$ genomic DNA with HindIII (FIG. 4), thus confirming integration of the GUS-encoding gene construct in the plant genome. Integration of the nptII gene into the $T_0$ plant genome was also confirmed by Southern blotting using nptII as a probe (data not shown). The molecular analysis of seedlings derived from one of the crosses between $T_0$ plants and non-transgenic breeding line (b.l.) 13261 is shown in FIG. 5. nptII PCR amplification followed by Southern blotting using nptII as a probe yielded a DNA fragment of the expected size (0.8 kb) in all analyzed kanamycin-resistant $T_1$ seedlings (FIG. 5) and not in controls (FIG. 5, lane C). Similarly, uidA PCR amplification of these $T_1$ seedlings followed by hybridization with uidA probe yielded a DNA fragment of the expected 0.53 kb in all cases (data not shown).

The applicability of the transformation procedure was also assessed with another two, genetically unrelated, commercially highly successful cultivars—Desio and Eilat, which had been used in transient transformation experiments. The efficiency of selection for these varieties was essentially identical to that detailed for cv. White Sim and overall transformation efficiencies of 13% and 18% (transgenes out of total inoculated explants) were obtained for cvs. Desio and Eilat, respectively. The transgenic nature of these plants was confirmed by Southern blot analysis (data not shown). Interestingly, the overall efficiencies of stable transformation for the three analyzed varieties were in good agreement with the frequency of transient transformation events (see FIG. 2).

II. rolC Transgenic Carnation

A. Materials and Methods

1. Gene Construct and Plant Genetic Transformation.

A 1.46-kb XbaI fragment from plasmid pUC18-CaMV35S-rolC (13), carrying the *A. rhizogenes* rolC gene (FIG. 6) driven by the CaMV 35S RNA promoter, was inserted into the XbaI-predigested pCGN1559 (McBride, K. E. and K. R. Summerfelt. 1990. Improved binary vectors for *Agrobacterium*-mediated plant transformation. Plant Mol. Biol. 14:269–276.) binary plasmid to create the binary plasmid pAMrolC. pAMrolC contains the nptII selection gene (coding for neomycin phosphotransferase II (NPTII); Beck, E., G. Ludwig, E. A. Auerswald, R. Reiss, and H. Schaller. 1982. Nucleotide sequence and exact location of the neomycin phosphotransferase gene from transposon Tn5. Gene 19:227–336) also driven by an 35S promoter. The plasmids pCGN7001 (Comai et al., 1990) (a control plasmid essentially identical to pCGN1559, but carrying the uidA gene coding for β-glucuronidase (GUS) driven by a mannopine synthetase (MAS) promoter and the nptII gene driven by the 35S promoter) and pAMrolC were transferred to *A. tumefaciens* strain AGLO (Lazo, G., P. Stein, and R. Ludwig. 1991. A DNA transformation-competent *Arabidopsis* genomic library in *Agrobacterium*. Bio/Technology 9:963–967) and used to transform *Dianthus caryophyllus* L. cv. White Sim as described above. Eighteen independent pAMrolC transformants were obtained, of which three rolC-transgenic lines (R-1, R-2 and R-3) were studied in more detail. The transgenic origin of the uidA-expressing control lines, which were phenotypically and morphologically indistinguishable from non-transformed plants, was previously confirmed as described above.

2. Southern and Northern Blot Analyses.

The cetyltrimethylammonium bromide (CTAB) extraction procedure and a TRI-REAGENT™ extraction kit (Molecular Research Center, Inc., Cincinnati, Ohio) were employed for DNA and RNA extraction, respectively, from leaves of greenhouse-grown plants, as described previously.

DNA (10 μg) was digested with HindIII and electophoresed through a 1% agarose gel using Tris-borate buffer (containing 1.3 M Tris, 0.7 M boric acid and 24.5 mM EDTA, pH 8.4). HindIII is a unique restriction site within the T-DNA fragment, 5' to rolC. Gels were stained with ethidium bromide and photographed under ultraviolet light. Total RNA (10 μg) was electrophoresed through a 1.2% formaldehyde gel (Vishnevetsky, M., M. Ovadis, H. Izhaki, M. Levy, Y Libal-Weksler, Z. Adam, and A. Vainstein. 1996. Molecular cloning of a carotenoid-associated protein from *Cucumis sativus* corollas: homologous genes involved in carotenoid sequestration in chromoplasts. Plant J. 10:1111–1118.). DNA and RNA were transferred to a nylon membrane (Hybond N+; Amersham, UK) by capillary blotting as described by Maniatis et al. (1982). The 0.76-kb SalI fragment from plasmid pUC18-CaMV35S-rolC, representing the 3' prime end of the rolC gene, served as a probe for that gene. Probe-labeling, and prehybridization and hybridization of Southern and northern blots were performed as described above. The blots were visualized by exposure to Agfa Curix PR2 film at –70° C. for 5 to 20 h with an intensifying screen.

3. Hardening of Tissue-Culture Plants and Establishment of Plants in the Greenhouse.

About 3-cm long, rooted plantlets were removed from the in vitro culture medium and their roots were cleaned of agar. The plantlets were then transferred to plastic planters filled with water-saturated no. 4 perlite (Agrical, Kibbutz Habonim, Israel) and kept for 2 weeks on a heated rooting table in a greenhouse under intermittent mist (misting cycles of approximately 3 min every half hour). The plantlets were then transferred to a no. 0.8 volcanic rock (Tof Marom Golan, Marom Golan, Israel) mixture and further grown for 4 weeks in the same rooting greenhouse. Hardened plants were then transferred to a regular greenhouse and 4 weeks later they were decapitated to allow breaking and elongation of axillary shoots. These plants served as the source for standard stem cuttings for all further experiments.

4. Assessment of Developmental Traits in the Greenhouse.

To evaluate the rooting performance of transgenic plants, stem cuttings, either directly or following dipping in 0.6% (w/w) indole-3-butyric acid (IBA) containing commercial rooting powder (Hormoril® T-6, Asia Rizel, Rarnat Gan, Israel), were planted in either no. 4 perlite or a rooting mixture (50% v/v no. 4 perlite, 10% v/v no. 2 perlite, 20% v/v slurry and 20% v/v peat). The stem cuttings (50 cuttings per line) were grown for 3 weeks on heated rooting tables. The cuttings planted in perlite only were then gently pulled and washed of rooting mixture. The root system was dissected, dried at 65° C. for 48 h and weighed.

Figure 7:
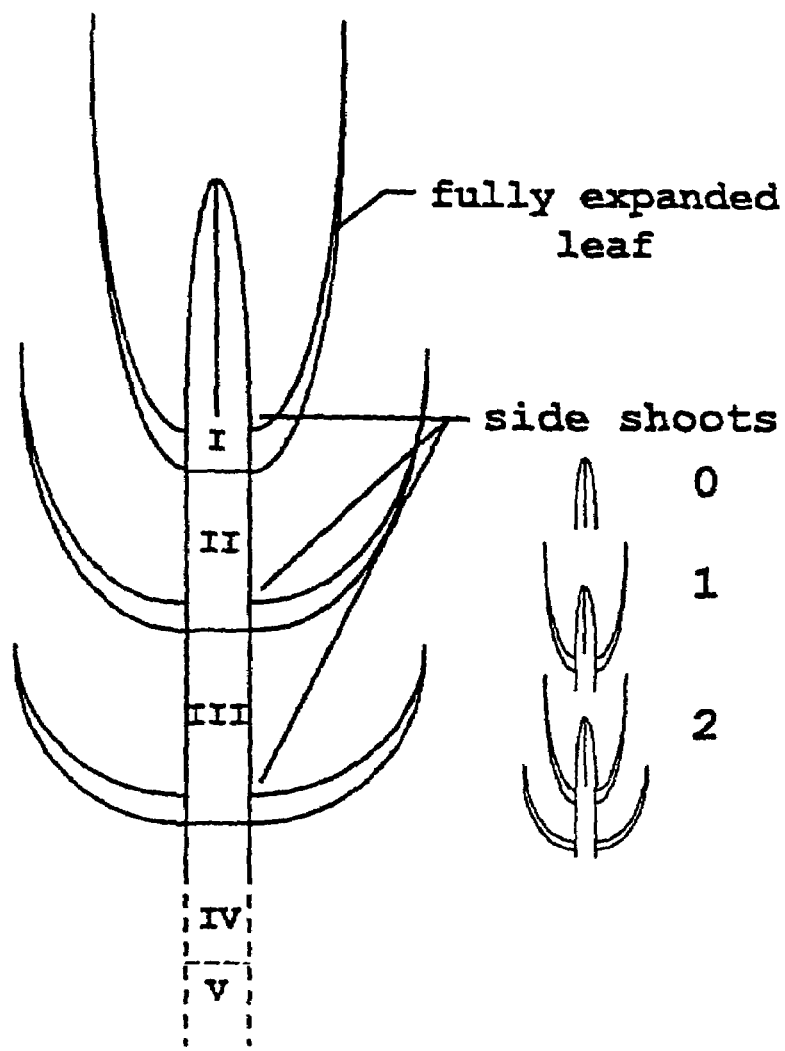

Stems cuttings dipped in Hormoril® and rooted in peat mixture were also transferred to no. 0.8 volcanic rock mixture for growth under regular greenhouse conditions, in order to establish mother plants for further clonal propagation. Four weeks after transfer to the greenhouse, plants were decapitated to allow for axillary bud development. Stem cuttings with at least three internodes, originating from the breaking and elongation of the axillary buds, were then harvested from the mother plants (40 plants per line) ca. every 4 weeks. A total of five harvest cycles was performed and the number of stem cuttings determined. In addition, the number of internodes in the stem cuttings obtained from the first harvest cycle was determined. Side shoots developing on these cuttings were also characterized as to their dry weight and the number of open leaves (FIG. 7).

Plant height at flowering was measured from the soil line to the top of the main flower bud on the flowering stem. The number of petals per flower bud, their length and dry weight were measured from flowers at anthesis, during the flowering season (November 1998–March 1999). The vase life of flowers with a 50-cm-long stem was measured in distilled water, at 20° C., under a 12-h photoperiod using cool white light (60 μmol $m^{-2}s^{-1}$).

B. Results

1. Confirming the Transgenic Nature of Selected Lines.

Figure 8:
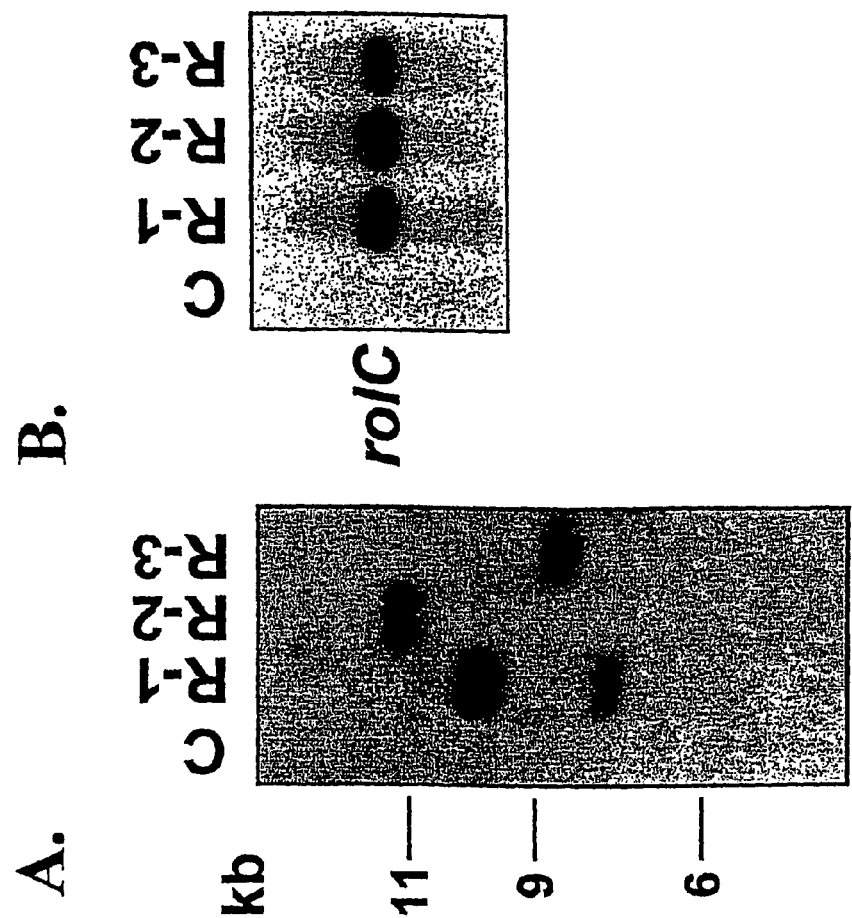

Transgenic plants were generated following two regeneration and selection cycles under high kanamycin pressure as described previously. All rolC- and control, uidA-transgenic plants exhibited high resistance to kanamycin, and the latter also exhibited strong GUS expression in all their organs. rolC-transgenic plants (18 independent lines) were screened in vitro for phenotypic alterations which included autonomous root growth in hormone-free media, axillary bud breakage, increased growth rate and altered internode length. Out of 18 lines exhibiting altered morphology, three independent lines (R-1, R-2 and R-3) were selected, hardened and transferred to the greenhouse for further study. Southern blot analysis of HindIII-digested DNA revealed integration of the rolC gene in all three selected lines (FIG. 8A). Northern blot analysis revealed the expression of rolC, driven by the constitutive 35S promoter, in these three lines (FIG. 8B), thus confirming their transgenic nature.

2. Yield and Morphology of Stem Cuttings from rolC-Transgenic vs. Control Plants.

Figure 9:
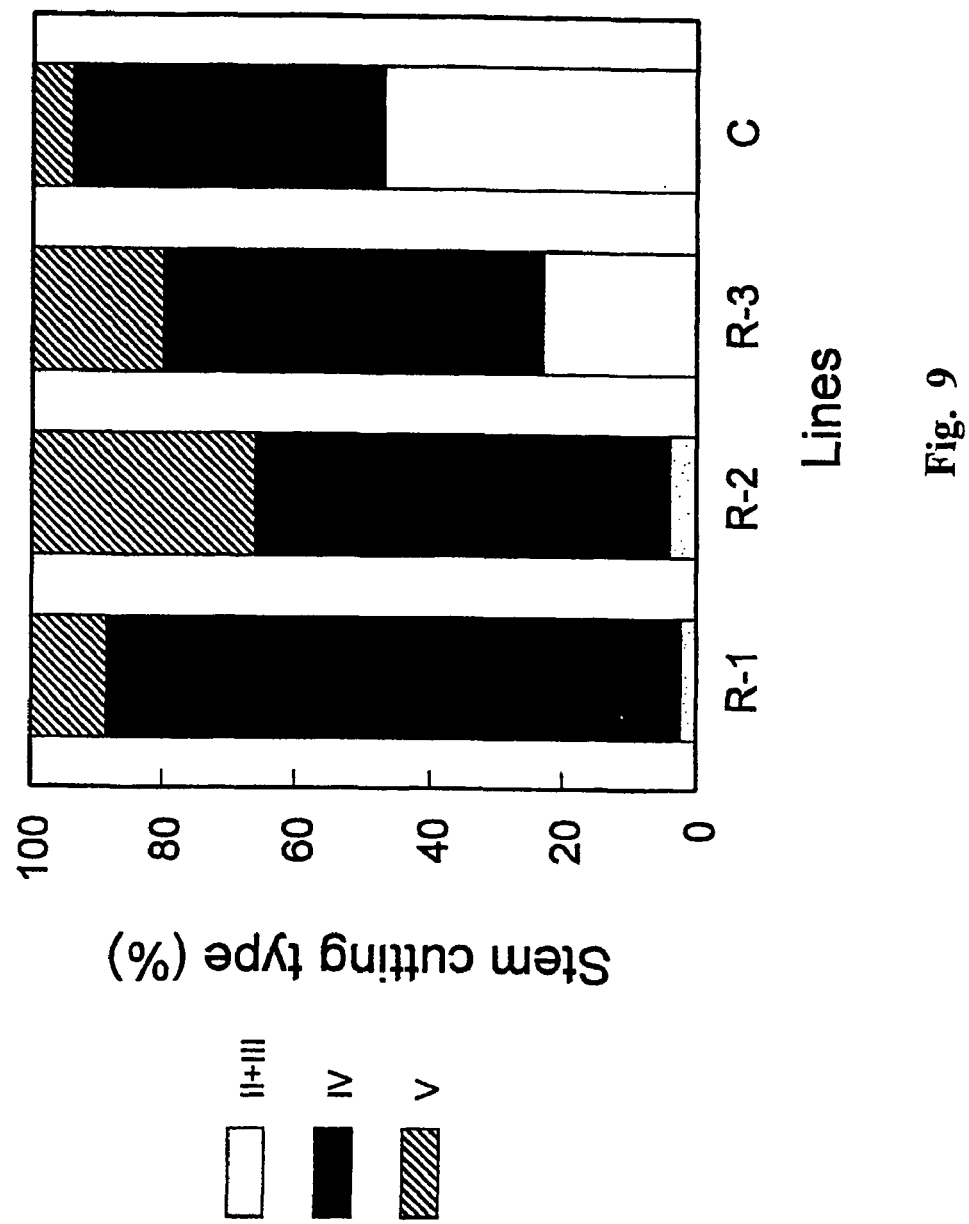

Stem cuttings were collected from rolC- and GUS-transgenic (control) carnation plants and classified, by developmental stage, based on the number of internodes per cutting (FIG. 7). About 50% of all stem cuttings from GUS-transgenic plants were of type III (three internodes), and only ca. 6% were of type V. In contrast, up to 97% of the rolC-transgene cuttings were of types IV and V (FIG. 9). Furthermore, the overall yield of cuttings per mother plant was up to 40% higher in rolC transgenes than in control plants (Table 2).

TABLE 2

Stem-cutting yield and properties in rolC-transgenic and control carnation plants.

| | | Side shoots | | |
|---|---|---|---|---|
| Stem cuttings | | Dry weight[b] | Open pairs of leaves[c] | |
| Line | Yield[a] (no.) | (positions 4 and 5) (mg) | position 4 (no.) | position 5 |
| R-1 | 23 ± 2 | 47 ± 1 | 1.6 ± 0.1 | 2.0 ± 0 |
| R-2 | 21 ± 1 | 44 ± 2 | 1.6 ± 0 | 1.8 ± 0.1 |
| R-3 | 21 ± 1 | 36 ± 1 | 1.1 ± 0.1 | 1.4 ± 0.2 |
| C | 16 ± 2 | 29 ± 3 | 0 | 0 |

[a]Stem cuttings were harvested a total of five times at 3- to 5-week intervals. An average number of stem cuttings ± SE per harvest per mother plant is presented.
[b]Average weight of side shoot ± SE, at positions 4 and 5, per stem cutting.
[c]The average number of open pairs of leaves ± SE per side shoot at positions 4 or 5 is presented.

To further characterize type IV and V stem cuttings, they were dissected and side shoots, developed from axillary buds, were weighed and their developmental stage ranked (FIG. 7, Table 2). Side shoots of rolC-transgenic stem cuttings exhibited an up to 1.5-fold higher dry weight than those originating from control plants (Table 2). Relative to control plants, the side shoots from rolC transgenes were much more developed (Table 2). In rolC transgenes, the average number of open leaf pairs on the side shoots at the 5th position ranged from 1.4 to 2.0. In line R-1, all side shoots at the 5th position had two open pairs of leaves. Furthermore, side shoots at the 4th position in all rolC transgenes averaged at least one pair of open leaves. In contrast, in control plants all side shoots developing at the 4th or 5th positions were without open leaves (Table 2).

3. Rooting Ability of rolC-Transgenic Carnation Plants.

Figure 10:
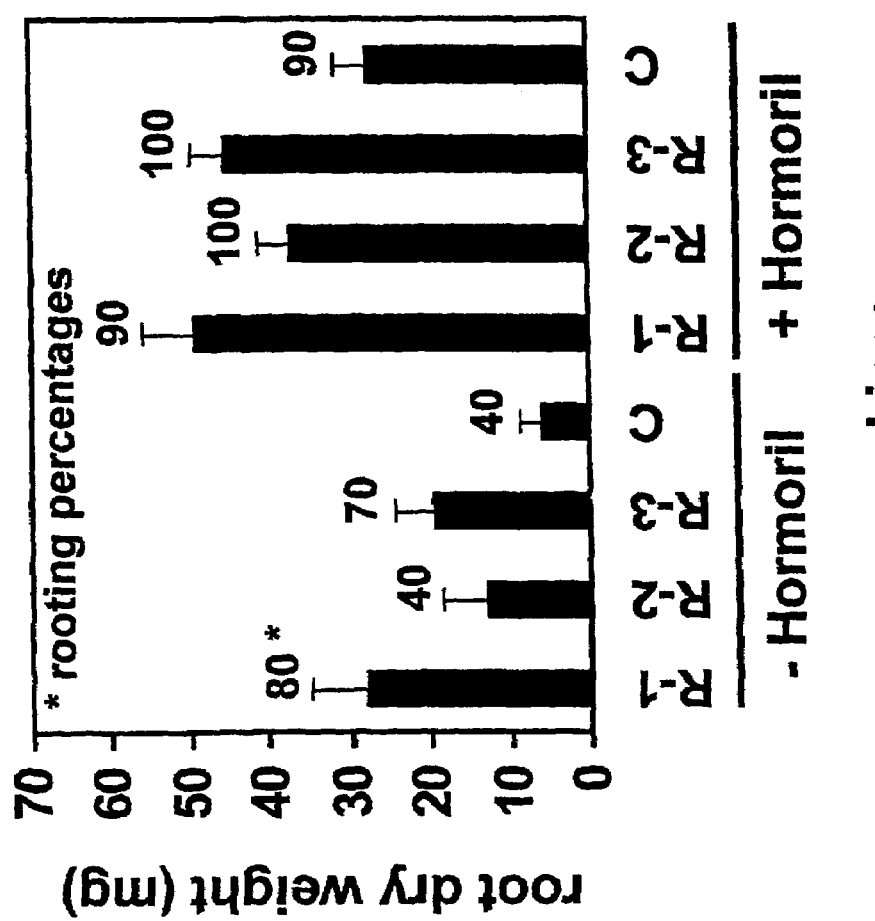
Figure 11A:
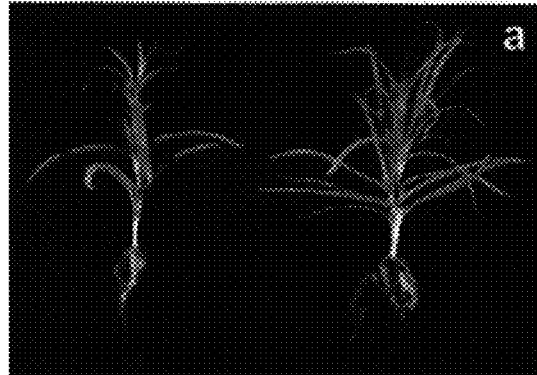
Figure 11B:
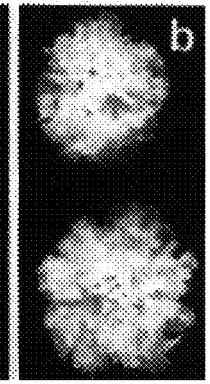
Figure 11C:
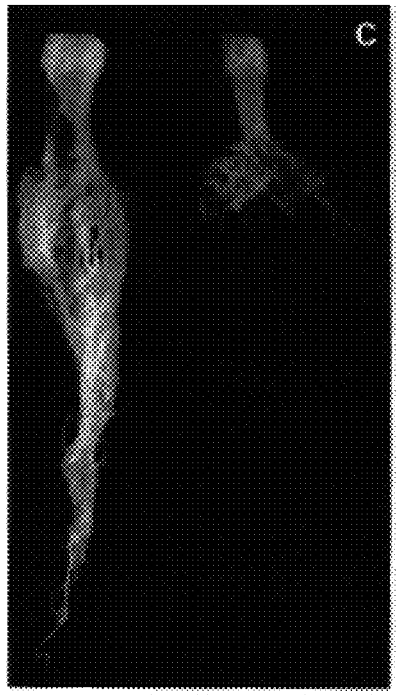
Figure 11D:
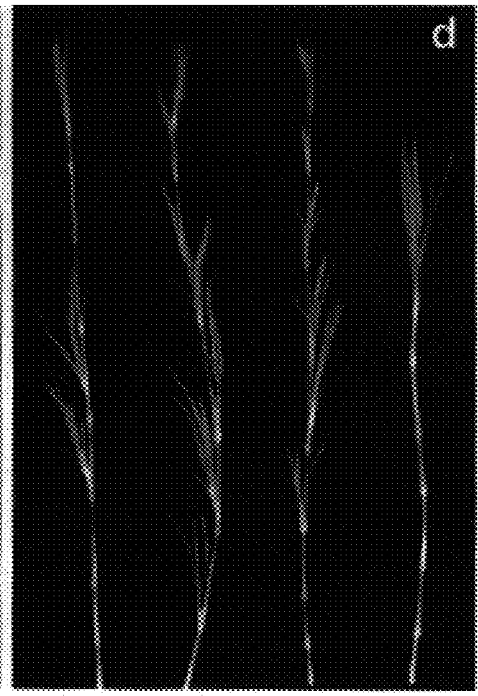

When stem cuttings were not treated with auxin (Hormoril® rooting powder), control (GUS-transgenic) cuttings yielded short and undeveloped adventitious roots, whereas rolC-transgenic cuttings developed a dense root system with a high dry weight mass, ca. two to five times higher than that of the control cuttings (FIGS. 10, 11). Moreover, the percentage of cuttings developing roots out of the total number of cuttings was ca. two times higher in R-1 and R-3 plants than in controls. In fact, nontreated stem cuttings of line R-1 exhibited root-system structures and dry weights similar to those of control plants treated with rooting powder (FIGS. 10, 11). The enhanced rooting ability of rolC transgenes vs. controls was also apparent following treatment of the cuttings with Hormoril®: rolC transgenes developed up to twice the root mass of control cuttings. Moreover, while a period of ca. 3 weeks was essential for the rooting of control carnation stem cuttings, a shorter period of only 2 weeks was required before rolC-transgenic carnation stem cuttings could be transferred for further development to standard greenhouse conditions.

4. Plant Growth and Flower Development.

To further assess the growth habits of rolC-transgenic and control (GUS-transgenic) plants, they were grown to flowering in the greenhouse. rolC transgenes developed a higher number of shoots and a more elaborate root system than control plants (FIG. 11). Furthermore, during the 5-month flowering season, the average number of flowering stems per mother plant in R-3 rolC transgenes was three times that in control plants (9.4±1.8, 3.2±1.0), two and two-and-a-half times for R-1 and R-2 (7.2±1.4, 8.1±1.7). The average number of flower buds on flowering stems was essentially the same (4.5±0.5 flowers/stem) in rolC and control plants.

The height of the flowering stems of rolC transgenes was similar to that of control plants, being 85±5, 87±4 and 95±6 vs. 75±5 cm in R-1, R-2, R-3 and control plants, respectively. Time to flowering was essentially identical in rolC transgenes and control plants, ca. 14 weeks after decapitation of mother plants. Flower vase life of control and rolC transgenes was also the same (12±2 days). An assessment of flower size during the flowering season revealed that R-1 and R-3 transgenic flowers are essentially identical to control ones, in all analyzed parameters, i.e. dry weight, petal number and size. R-2 transgene flowers were smaller (FIG. 11) due to a smaller number of petals: 410±54 mg flower dry weight with 35±3 petals (24±3 mm in length) as compared to 696±53 mg dry weight with 55±2 petals (33±3 mm in length) in control flowers. Crosses between R-1, R-2, R-3 and non-transformed male carnation plants revealed that introduction of the rolC gene does not affect the flower's female fertility (not shown). The effect of rolC on male fertility could not be tested, because White Sim, the cultivar used in this study to generate transgenes, is male-sterile.

III. Antisense Suppresion of fht

A. Materials and Methods

1. Plant Transformation and Vector Construction

The cDNA sequence of the fht gene is shown in FIG. 12. A carnation partial fht cDNA clone (1 kb) was isolated by PCR of reverse-transcribed poly (A)$^+$ RNA, using specific primers according to the sequence in GenBank (X70378). This fragment was subcloned in antisense orientation (FIG. 13) between the CaMV 35S promoter and nos terminator in pJD330 (Broido, S., Loyter, A. & Vainstein, A. Transient expression of photosynthetic genes in trasfected albinoid petunia protoplasts and correct processing of newly synthesized chloroplast-destined polypeptides. *Physiol. Plant.* 88, 259–266 (1993)) to create pJD-anti-fht. An XbaI fragment from pJD-anti-fht was then cloned into the binary vector pCGN1559 (Comai, 1990) to create pAM-anti-fht. The gene construct was transferred to carnation cv. Eilat via cocultivation of stem explants, as described above, with *Agrobacterium tumefaciens*, AGLO containing pAM-anti-fht.

2. Molecular and Biochemical Analysis.

For northern analysis, RNA was extracted from petals and samples (10 µg) were electrophoresed through an agarose gel, transferred to a membrane and probed with $^{32}$P-labeled fht and dfr cDNAs as described previously (Vishnevesky, M. et al). For RT-PCR analysis (de Lang, P., de Boer, G.-J., Mol, J. N. M. & Kooter, M. Conditional inhibition of -glucuronidase expression by antisense gene fragments in petunia protoplast. Plant Mol. Biol. 23, 45–55 (1993)), RNA samples treated with DNase were reverse-transcribed with M-MLV reverse transcriptase, using strand-specific fht and chs (sense and antisense) primers. The resultant cDNAs were PCR-amplified using a mixture of both sense and antisense primers. The amplified product was analyzed by Southern blotting as described above, using $^{32}$P-labeled fht and chs.

Carnation cDNA clones of chs and dfr were isolated, as described above for FHT, by PCR using specific primers according to their sequences in GenBank: chs (Z67982), dfr (Z67983). Primers used were: 5' CCC AAA ACG CTC ACT TCA CT 3' (SEQ ID NO:6) and 5'CCA AGC CCA TCT AAG CAA GT 3' (SEQ ID NO:7) for fht; 5' GGG CCG ATG GTC CTG CTA CTA T 3' (SEQ ID NO:8) and 5' ACG CGC TCG ACA TGT TCC CAA A 3' (SEQ ID NO:9) for chs; 5' TGT GAA TGT CGA AGC GAC TC 3' (SEQ ID NO: 10) and 5' TTG AAT TTG GTG GGG ACA TT 3' (SEQ ID NO:11) for dfr.

Feeding experiments (Deroles, S. C. et al. An antisense chalcone synthase cDNA leads to novel colour patterns in lisianthus (*Eustoma grandiflorum*) flowers. *Mol. Breed* 4, 59–66 (1998)) were performed with detached petals, incubated for several hours in 1 mg/ml dihydroquercetin in 5% methanol. FHT activity was assayed using petal extracts (Britsch, L. & Grisebach, H. Purification and characterization of (2s)-flavanone 3-hydroxylase from *Petunia hybrida*. *Eur. J. Biochem.* 156, 569–577 (1986)) and flavonoid analysis was performed by TLC (Harborne, L. B. *Comparative Biochemistry of the Flavonoids* (Academic Press, New York, 1967)).

3. Headspace GC-MS Analysis and Fragrance Tests.

Detached flowers at anthesis were sealed in a 35-ml glass tube for 30 min and volatile compounds were trapped for 10 min using polydimethylsiloxane-coating solid-phase-microextraction (SPME) fiber assembly (Supelco Inc., Bellefonte, Pa.). As a blank, trapping was performed in sealed tubes without flowers. Compounds were analyzed by SPME headspace GC-MS (Helsper, J. P. F. G., Davies, J. A., Bouwmeester, H. J., Krol, A. F. & van Kampen, M. H. Circadian rhythmicity in emission of volatile compounds by flowers of Rosa hybrida L. cv. Honesty. Planta 207, 88–95 (1998)) (Varian Star 3400 CX GC equipped with a 30 m×0.25 mm ID, DB-5MS column and interfaced with a Varian Saturn 3 MS). The fiber was manually placed into a 1077 splitless injector for 3 min (injector temperature was 210° C.). Helium served as the carrier gas and GC temperature was programmed as follows: 3 min at 40° C., increased to 220° C. at 15° C. min$^{-1}$ and then 5 min at 220° C. Ionization energy was 70 eV. Each compound was tentatively identified (>95% match) based on the Wiley library (Wiley registry of mass spectral data, $6^{th}$ edition, F. W. McLafferty, 1994, J. Weiley & Sons, Inc). To confirm identification, standard compounds were used to match GC retention times and MS spectra. Authentic compounds were obtained from Sigma Chemical Co. (St. Louis, Mo.).

Paired-comparison fragrance test (O'Mahony, M. *Sensory Evaluation of Food* (Marcel Dekker, New York, 1986)) was performed with 45 panelists. An intensity category scaling test (Meilgaard, M., Civille, G. V & Carr, T. B. *Sensory Evalvuation Techniques* (CRC Press Inc, Boca Raton, Fla., 1991)) (1–5 scale, 1 for no fragrance, 5 for very intense fragrance) was performed with 20 panelists.

B. Results

The flowers of carnation cv. Eilat have dark orange petals with reddish edges (FIG. 14a). The enzyme flavonoid 3',5'-hydroxylase is lacking in carnation, and in cv. Eilat, flavonoid 3'-hydroxylase (F3'H) is inactive: only pelargonidin and the yellow isosalipurposide (ISP) are accumulated. Following transformation of cv. Eilat with antisense fht, 14 individual transgenic plants were regenerated and grown to flowering in the greenhouse. All plants developed and flowered normally and six of them exhibited color modifications ranging from attenuation to complete loss of the orange/reddish color (FIGS. 14b–d). A complete loss of orange/reddish color and the production of yellow/cream flowers, accumulating ISP and only traces of pelargonidin, was observed in two independent anti-fht transformants (FHT-11 and FHT-14, FIGS. 14c and 14d, respectively). Transformation of cv. Eilat with the identical vector carrying the gus reporter gene instead of fht led only to transgenes with true-to-type flower color.

Since, like many commercial carnation varieties, cv. Eilat is sterile, the inheritance of color modification could not be analyzed. Southern blot analysis confirmed the presence and integration of anti-fht gene construct into the genome of the transgenic plants (data not shown). Northern blot analysis (FIG. 15a) revealed dramatic suppression of fht transcript in transgenes FHT-11 and FHT-14, in contrast to controls and transgene FHT-33. To further detail the suppression of the fht gene, RT-PCR analysis of the endogenous and transgenic fht transcripts was performed (de Lang, et al, 1993) using strand-specific primers. Petals of FHT-11 transgenes, which exhibited a dramatically modified phenotype (FIG. 14c), did not accumulate detectable levels of sense fht transcript (FIG. 15b). In contrast, petals of transgenic line FHT-33, which showed only minor color alterations (FIG. 14b), accumulated relatively high levels of sense transcript. The level of fht antisense transcript was much lower in FHT-11 than in the FHT-33 transgene. In control flowers, as expected, only sense transcript could be detected. Analysis of chs transcript, used as a control, yielded the expected results, i.e. similar levels of sense transcript were detected in all analyzed plants. Analysis of FHT enzyme activity in petals of FHT-11 revealed no detectable activity, in contrast to strong FHT activity in control plants (FIG. 15c). This blockage in the anthocyanin biosynthetic pathway could be complemented by feeding detached petals with the product of the FHT enzyme, dihydroquercetin (FIG. 14e).

During the course of a 2-year field test, we observed that flowers of two independent transgenic plants (FHT-11 and 14) were more fragrant than non-transformed or GUS-transgenic controls. The enhanced fragrance was observed in flowers with strongly reduced anthocyanin accumulation, but not in FHT-33 or other transgenic lines exhibiting less dramatic reductions in anthocyanin levels. To confirm the observation that the anti-fht transgenes (FHT-11 and FHT-14) were more fragrant than controls, a paired-comparison fragrance test was performed. The overall fragrance intensity of transgenic FHT-11 flowers was significantly higher (p=0.001) than that of control flowers. Furthermore, an intensity category scaling test revealed a highly significant difference (p<0.001, paired t-test) in the intensity scores of transgenic FHT-11 (mean±SE=3.2±0.3) vs. control (1.3±0.2) flowers. Essentially identical results were found for transgene FHT-14.

To further characterize the scent of transgenic and control flowers, gas chromatography-mass spectroscopy (GC-MS) headspace analyses were performed. Cv. Eilat and transgenic plants FHT-11 and 14 were grown in the greenhouse side by side, and flowers at anthesis were collected simultaneously and immediately analyzed. Among the major volatiles generated by carnation flowers, various known fragrance compounds were found. These compounds represented different metabolic pathways: the terpenoid trans-caryophyllene, the fatty acid derivative hexanoic acid, and the benzoic acid derivative methylbenzoate (FIG. 16).

In all analyses performed during the 4-month-flowering period (20 independent analyses, performed on different dates, with four flowers per line), the level of methylbenzoate was higher by a factor of 10 to 100 (varying with environmental conditions and sampling times) in flowers of FHT-11 and 14 relative to controls. The levels of trans-caryophyllene and hexanoic acid were not affected by the anti-fht transgene. Hence, essentially complete inhibition of dihydroflavonol biosynthesis by fht antisense diverts metabolic flow towards the biosynthesis of benzoic acid derivatives, which also originate from the phenylpropanoid pathway (FIG. 17). Methylbenzoate is a known fragrance compound produced by many flowers, and therefore it is not unreasonable to propose that this compound is responsible, at least in part, for the enhanced fragrance in the transgenic plants. To this end, both flower fragrance and methylbenzoate levels were increased in control plants following feeding with the fht substrate, naringenin (not shown).

The invention claimed is:

1. A method for enhancing the fragrance of a plant comprising expressing in said plant an antisense oligonucleotide targeting the fht gene and selecting a transgenic plant with enhanced fragrance.

2. The method according to claim 1, where said plant is a carnation.

3. The method according to claim 1, wherein said antisense oligonucleotide suppresses the expression of the fht gene.

4. A transgenic carnation plant, wherein the fragrance of said plant has been enhanced by expressing in said plant an antisense oligonucleotide targeting the fht gene of said plant.

5. The method according to claim 1, wherein said plant is a carnation (*Dianthus* L.) plant, and the method is conducted by (a) preparing a stem explant from a carnation cutting; (b) wounding said explant by microprojectile bombardment; (c) cocultivating said wounded explant with *Agrobacterium* comprising a DNA molecule under conditions of exposure to dark followed by light to transform the carnation plant genome, wherein said DNA molecule expresses in said plant an antisense oligonucleotide targeting the fht gene; (d) excising a shoot from said cultivated wounded explant and removing a leaf from said shoot; and (e) culturing said leaf to obtain a transgenic plant transformed with said DNA molecule.

6. The method according to claim 5, wherein said antisense oligonucleotide suppresses the expression of the fht gene.

7. The method according to claim 5, wherein said conditions of dark followed by light comprise 2–4 days in the dark followed by 1–4 days in the light.

8. The method according to claim 5, wherein said carnation cutting is a stem cutting with four to ten fully mature leaves.

9. The method according to claim 8, wherein leaves and shoot apices are removed from said stem cuttings and two to five primary nodes are isolated.

10. The method according to claim 5, wherein said microprojectile bombardment comprises accelerating tungsten particles at said stem explant.

11. The method according to claim 10, wherein said tungsten particles are accelerated at a pressure of 1300–2000 psi and at a distance of 3–12 cm from said explant.

12. The method according to claim 5, wherein said wounded explant is cocultivated with *Agrobacterium* in a medium supplemented by α-naphthalene acetic acid (NAA) and 1-phenyl-3(1,2,3-hiadiazol-5-yl)-urea.

13. The method according to claim 5, wherein the leaf of said excised shoot is cultured in a medium supplemented by NAA and 6-benzylaminopurine.

14. A transgenic carnation plant obtained by the method of claim 5.

* * * * *

SEQUENCE LISTING

<160> NUMBER OF SEQ ID NOS: 11

<210> SEQ ID NO 1
<211> LENGTH: 987
<212> TYPE: DNA
<213> ORGANISM: Agrobacterium rhizogenes

<400> SEQUENCE: 1

```
atggctgaag acgacctgtg ttctctcttt ttcaagctca aagtggagga tgtgacaagc      60
agcgatgagc tagctagaca catgaagaac gcctcaaatg agcgtaaacc cttgatcgag     120
ccgggtgaga atcaatcgat ggatattgac gaagaaggag ggtcggtggg ccacgggctg     180
ctgtacctct acgtcgactg cccgacgatg atgctctgct tctatggagg gtccttgcct     240
tacaattgga tgcaaggcgc actcctcacc aaccttcccc cgtaccagca tgatgtgact     300
ctcgatgagg tcaatagagg gctcaggcaa gcatcaggtt ttttcggtta cgcggatcct     360
atgcggagcg cctacttcgc tgcattttct ttccctgggc gtgtcatcaa gctgaatgag     420
cagatggagc taacttcgac aaagggaaag tgtctgacat cgacctcta tgccagcacc      480
cagcttaggt tcgaacctgg tgagttggtg aggcatggcg agtgcaagtt tgcaatcggc     540
taatggttag tcgatgggct gacgagtttg atgtcaggag aagctgagtg tgtcacttgt     600
ttccctttaa gaagtattaa tgtaataaaa atcaagatct ggtttaataa ctggatactt     660
gatttcatcg cgcttttttt gaataaatgt ttgttgtctt gactttaaga tatcctttga     720
aatttgcgtt attcgtattt cgcttttggt tatttccaaa agactttgct cagtaagatc     780
aaacgtttgt atttctccgg gccacaatat ttgacctata tgcactggcc cacgcgccgc     840
aatagatgaa aattgccaaa attagctatc ggtcttctga aaagaagggc cgacatgttt     900
tcatagacca tgcaaagtca tactacctga aactgataaa taacgacaaa gaaagtagcc     960
tatttaaaag tcgctatagc atgaatt                                         987
```

<210> SEQ ID NO 2
<211> LENGTH: 1360
<212> TYPE: DNA
<213> ORGANISM: Dianthus caryophyllus

<400> SEQUENCE: 2

```
actatatctt aaatattcac aacattataa cataagcttc aaaataacat tattccgata      60
tttacgtaat ataatacgta tcatattagg gtacattcat tttatcaact acgactgcat     120
attgttagac agtctcatat atacgcataa aaaatggtcg ctgaaaaacc caaaacgctc     180
acttcactag aaggggacga taaattgaac tcgaattttg ttagggacga ggatgaacgt     240
ccgaaagtgg cgtataatga gtttagcaat gatattccgg tgatatctct tgctggtata     300
gatggtgaaa aaggggtgaa atatgtcgga agattgttg aggcgtgtga agattggggg     360
attttttcaag tggttgatca cggtgttggt gacgatctta ttgctgatat gactcggttg     420
gctcgtgaat ttttcgctct cccggcagaa gagaagctcc gatttgatat gtctggtggt     480
aaaaagggcg gttttatcgt gtcgagtcat cttcaggttc aatcaacagg gagaagtagt     540
gcaggactgg agggaaatcg tgacgtattt ctcatacccg acgaactcaa gggactacac     600
aagatggcca gacaaaccag agggttggat aaaggtcaca gaggaataca gcaacaagtt     660
aatgacctta gcatgtacac ttttaggtgt actttctgaa gccatgggtt tagaattaga     720
ggcacttact aaagcttgtg ttgatatgga ccaaaagatt gtggttaatt actaccctaa     780
```

```
gtgccctcaa cctgacctta ctttagggct caagaggcac accgaccccg ggactataac    840
cctcctcctt caggaccaag tcggcggtct tcaggccact cgtgacggtg gtaaaacttg    900
gattaccgtg cagccggttc ccgtgcctt cgttgttaac cttggtgatc atggtcatgt     960
tcggcgaaaa atggccaaag accttgagat cgcccgtcat aagaggcttg ctaaagagga   1020
aatgcctttt aaagagttgg acgaggccaa gtttgagtcc aaatctattg accaaatact   1080
tgcttagatg ggcttggttt ggtttcatta tattaaattt attattatta ttatttattg   1140
catttgatat gatatgattg gaaataaaag agagattgtt tgtgataatt tgtgtgatta   1200
ttatatcact aagttatggc tttaatttgt ggtatgttgg gaattatata tttagttttg   1260
tgtgaagaat atatgattta aagttaaaaa aaaaaatgat ttgttatatg atttacttgt   1320
aaggttataa ggttatattt attgttcgag tttgcgtata                         1360

<210> SEQ ID NO 3
<211> LENGTH: 929
<212> TYPE: DNA
<213> ORGANISM: Dianthus caryophyllus

<400> SEQUENCE: 3
ccaagcccat ctaagcaagt atttggtcaa tagatttgga ctcaaacttg gcctcgtcca    60
actctttaaa aggcatttcc tctttagcaa gcctcttatg acgggcgatc tcaaggtctt   120
tggccatttt tcgccgaaca tgaccatgat caccaaggtt aacaacgaag gcaccgggaa   180
ccggctgcac ggtaatccaa gttttaccac cgtcacgagt ggcctgaaga ccgccgactt   240
ggtcctgaag gaggagggtt atagtcccgg ggtcggtgtg cctcttgagc cctaaagtaa   300
ggtcaggttg agggcactta gggtagtaat taaccacaat cttttggtcc atatcaacac   360
aagctttagt aagtgcctct aattctaaac ccatggcttc agaaagtaca cctaaaagtg   420
tacatgctaa ggtcattaac ttgttgctgt attcctctgt gacctttatc caaccctctg   480
gtttgtctgg ccatcttgtg tagtcccttg agttcgtcgg gtatgagaaa tacgtcacga   540 tttcctcca gtcctgcact acttctccct gttgattgaa cctgaagatg actcgacacg    600
ataaaaccgc cctttttacc accagacata tcaaatcgga gcttctcttc tgccgggaga   660
gcgaaaaatt cacgagccaa ccgagtcata tcagcaataa gatcgtcacc aacaccgtga   720
tcaaccactt gaaaaatccc ccaatcttca cacgcctcaa caatcttccg acatatttca   780 ccccttttt caccatctat accagcaaga gatatcaccg gaatatcatt gctaaactca   840
ttatacgcca ctttcggacg ttcatcctcg tccctaacaa aattcgagtt caatttatcg   900
tccccttcta gtgaagtgag cgttttggg                                     929

<210> SEQ ID NO 4
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 4
gaggctattc ggctatgact                                                20

<210> SEQ ID NO 5
<211> LENGTH: 20
<212> TYPE: DNA
<213> ORGANISM: Artificial Sequence
<220> FEATURE:
```

```
<223> OTHER INFORMATION: Synthetically generated primer

<400> SEQUENCE: 5
aatctcgtga tggcaggttg                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 6
cccaaaacgc tcacttcact                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 7
ccaagcccat ctaagcaagt                                                20

<210> SEQ ID NO 8
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 8
gggccgatgg tcctgctact at                                             22

<210> SEQ ID NO 9
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 9
acgcgctcga catgttccca aa                                             22

<210> SEQ ID NO 10
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 10
tgtgaatgtc gaagcgactc                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 11
ttgaatttgg tggggacatt                                                20
```